(12) United States Patent
Labrenz

(10) Patent No.: US 6,333,501 B1
(45) Date of Patent: Dec. 25, 2001

(54) METHODS, APPARATUS, AND ARTICLES OF MANUFACTURE FOR PERFORMING SPECTRAL CALIBRATION

(75) Inventor: James N. Labrenz, San Francisco, CA (US)

(73) Assignee: Perkin-Elmer Corporation, Foster City, CA (US)

(*) Notice: Subject to any disclaimer, the term of this patent is extended or adjusted under 35 U.S.C. 154(b) by 0 days.

(21) Appl. No.: 09/493,056

(22) Filed: Jan. 27, 2000

(51) Int. Cl.[7] .................................................. G01J 5/02
(52) U.S. Cl. .............................. 250/341.5; 250/339.09; 250/340
(58) Field of Search ............................ 250/341.5, 340, 250/343, 339.09, 339.01, 338.1, 336.1

(56) References Cited

U.S. PATENT DOCUMENTS

| | | |
|---|---|---|
| 4,631,687 | 12/1986 | Kowalski et al. . |
| 5,068,536 | * 11/1991 | Rosenthal ........................ 250/341.5 |
| 6,015,667 | 1/2000 | Sharaf . |

OTHER PUBLICATIONS

Thom M. Apostol, Calculus, *Multi–Variable Calculus and Linear Algebra, with Applications to Diffential Equations and Probability*, John Wiley–Sons, vol. II, 1969, pp. 22–30.

Aapo Hyvarinen, Survey on Independent Component Analysis, Laboratory of Computer and Information Science, Helsinki Univ. of Technology, 1999, pp. 1–35.

A.K. Jain, et al., Data Clustering: A Review, ACM, Inc., 1996, 1 page.

Achim E. Karger, et al., Multiwavelength Fluorescence Detection for DNA Sequencing Using Capillary Electrophoresis, Nucleic Acids Research, vol. 19, No. 18, Oxford University Press, 1991, pp. 4955–4962.

Fritz J. Knorr, et al., Separation of Mass Spectra of Mixtures by Factor Analysis, Analytical Chemistry, vol. 51, No. 8, Jul. 1979, pp. 1236–1241.

William H. Press, et al., *Numerical Recipes in C, The Art of Scientific Computing*, Cambridge University Press, Second Edition, 1998, pp. 650–655.

William H. Press, et al., *Numerical Recipes in C The Art of Scientific Computing*, Cambridge University Press, Second Edition, 1998, pp. 58–70.

Zhongbin Yin, et al., Automatic Matrix Determination in Four Dye Fluorescence–based DNA Sequencing, Electrophoresis, No. 17, pp. 1143–1150.

* cited by examiner

*Primary Examiner*—Hung Xuan Dang
(74) *Attorney, Agent, or Firm*—Finnegan, Henderson, Farabow, Garrett & Dunner, L.L.P.

(57) ABSTRACT

A system performs two types of spectral calibration. For the first type, the system collects data from monitoring an analytical separation of several spectrally-distinguishable molecular species and creates a data matrix from the collected data. Each element in the data matrix represents a signal intensity at a particular time and over a particular range of light wavelengths. The system then identifies regions in the data matrix that have spectral response characteristics of at least one of the molecular species, determines a set of pure component spectral responses from the identified regions, groups similar pure component spectral responses into clusters, determines a representative spectral response for each cluster, and correlates the representative spectral response for each cluster with one of the molecular species. For the second type of calibration, the system collects data from monitoring an analytical separation of multiple spectrally-distinguishable molecular species and creates a data matrix from the collected data. Each element in the data matrix represents a signal intensity at a particular time and over a particular range of light wavelengths. The system then identifies binary mixture regions within the data matrix, determines pairs of the binary mixture regions that contain one common spectral response, identifies a component that represents the one common spectral response using data in the determined pairs, groups the one common spectral response from each of the determined pairs into clusters, determines a representative spectral response for each cluster, and correlates the representative spectral response for each cluster with one of the molecular species.

100 Claims, 9 Drawing Sheets

METHODS, APPARATUS, AND ARTICLES OF MANUFACTURE FOR PERFORMING SPECTRAL CALIBRATION

BACKGROUND OF THE INVENTION

A. Field of the Invention

The present invention relates generally to spectral calibration and, more particularly, to spectral calibration resulting from monitoring a mixture containing multiple spectrally-distinguishable species.

B. Description of Related Art

Many materials express light when excited by incident light. The characteristics of expressed light in response to various excitation light wavelengths help identify the material. Different response spectra can also identify different properties of the material and may be used to differentiate components within a cell. To aid in the identification, cellular components, such as DNA fragments, are labeled with different fluorescent dyes that have distinct spectral responses, making the components spectrally distinct.

Spectral calibration estimates reference spectral profiles (i.e., reference spectra) of particular fluorescent dyes using a fluorescent separation system. Conventional approaches to spectral calibration measure the spectral profile of each fluorescent dye separately. These approaches result in reduced throughput and increased system complexity because they require N lanes on gel-based mediums and N separate runs on capillary-based mediums. Furthermore, with conventional reaction kit products, such as the PE Biosystems Big Dye Terminator™ kit, the reagents for the reactions (in this case, for DNA sequencing) are pre-mixed, making it impossible to perform separate dye-specific calibration runs using the actual reaction-kit products. This problem may therefore necessitate the manufacturing of special-purpose calibration kits and the design of a corresponding instrument calibration protocol in order to obtain the reference spectra in an automated way.

While this is feasible, it results in greater expense and/or greater complexity to the end-user. In addition, from a manufacturing standpoint, there is the added burden of quality control on the production of the calibration kits. For most applications, the reference spectra obtained using the calibration kit must match the "true" spectra exhibited by the target reaction kit products to a high degree of accuracy, usually to within 5% or less in terms of miscalibration error (see below). While meeting such a specification is certainly achievable, chemistry and/or manufacturing differences that distinguish the calibration-kit products from those generated using the target reaction kits provide a greater opportunity for the introduction of systematic miscalibration error. Examples may include (1) differences in the manner in which the dyes are chemically attached to the cellular components, and (2) the possible introduction of low levels of dye-label to fragment-size cross contamination in the manufacturing of the calibration kit products. In this regard, the "calibration kit" approach is in contradistinction to spectral calibration performed using dye-labeled cellular components (e.g., DNA) generated from the target reaction kits themselves, with the aid of additional automated data-processing algorithms.

A situation in which the spectra measured in a calibration run differ slightly from the spectra exhibited by the products of the target reaction kit leads to systematic error in subsequent production-run data processing. Typically, the calibration matrix is used in a first step of processing the raw fluorescence-intensity data in a procedure known as multicomponenting. Assume, for example, that the instrument collects fluorescence intensity values during each instance of measurement over several predefined ranges of light wavelength (i.e., virtual filters). The raw-data electropherogram constitutes the sequential collection of all such measurements made by the system during the electrophoresis run. Multicomponenting, then, consists of a matrix multiplication of each measurement "vector" by the inverse of the calibration matrix. If the number of virtual filters collected from the instrument is greater than the number of dye signals to be computed, the pseudo-inverse of the calibration matrix is used in place of the ordinary inverse. This process is intended to transform the intensity data from the vector space of relative intensity in each of the virtual filters to the vector space of relative dye-label concentrations in a way that is mathematically optimal in a least mean-squares sense.

The manifestation of calibration error in the multicomponenting process is a phenomenon known as "pull-up" or "pull-down" (PU/PD) in the transformed intensity data. In a region of an electropherogram where there exists a peak in a single dye-labeled component, PU/PD can exhibit a false peak or "negative peak" in one or more of the alternate dye signals. Given that a peak in one of the dye signals of the transformed data otherwise corresponds to the passage of a particular class of cellular component past the detection system, positive peaks in alternate colors may be interpreted by the subsequent analysis as representing a low-level presence of the corresponding dye-labeled component, when in fact there is none. This type of error can, therefore, introduce a signal indicating the false presence of another dye-labeled species.

Furthermore, should the miscalibration manifest itself as pull-down (negative peaks), heuristic algorithms typically used to determine the baseline (background) signal in each dye/color channel as a function of time may be adversely affected. This can then lead to further problems in the subsequent processing of the data, such as the appearance of additional false peaks due to band-pass filtering or deconvolution of elevated baseline regions, etc. Depending upon the quality of the data being processed, a low level of false peaks introduced by spectral miscalibration error may drastically lower the effective signal-to-noise ratio of the electrophoretic measurements.

If low-level peaks cannot otherwise be classified as real peaks or false ones, they will effectively define a threshold of true peak detection. Therefore, applications demanding a large dynamic range of detection may be adversely affected or rendered infeasible if the spectral calibration cannot be performed accurately. A good example of such an application is sequencing for polymorphism (heterozygote) detection. In such an application, heterozygous positions in a sequence are manifest as truly (or nearly) overlapping peaks in the electropherogram. Certain protocols, such as when pooling patient samples, demand a low threshold of detection and correspondingly large dynamic range.

Other examples where PU/PD systematic error can introduce classification errors in subsequent analysis include alelle identification for fragment analysis applications (e.g., GeneScan™). These types of error may adversely affect genetic mapping projects or Human Identification analyses.

As a result, a need exists for new approaches to spectral calibration that overcome the deficiencies of the conventional approaches.

SUMMARY OF THE INVENTION

Systems and methods consistent with the present invention address this need by performing spectral calibration concurrently for spectrally-distinguishable molecular species in a manner that is more accurate and more robust than conventional approaches.

In accordance with the purpose of the invention as embodied and broadly described herein, a system, in one implementation consistent with the present invention, performs spectral calibration. The system collects data from monitoring an analytical separation of several spectrally-distinguishable molecular species and creates a data matrix from the collected data. Each element in the data matrix represents a signal intensity at a particular time and over a particular range of light wavelengths or an approximated time-derivative of the signal intensity. The system then identifies regions in the data matrix that have spectral response characteristics of at least one of the molecular species, determines a set of pure component spectral responses from the identified regions, groups similar pure component spectral responses into clusters, determines a representative spectral response for each cluster, and correlates the representative spectral response for each cluster with one of the molecular species.

In another implementation consistent with the present invention, a computer-readable medium stores instructions executable by a processor for performing a spectral calibration method. The method includes collecting data from monitoring an analytical separation of multiple spectrally-distinguishable molecular species; creating a data matrix from the collected data, each element in the data matrix representing a signal intensity at a particular time and over a particular range of light wavelengths or an approximated time-derivative of the signal intensity; identifying regions in the data matrix having spectral response characteristics of at least one of the molecular species; determining a set of pure component spectral responses from the identified regions; grouping similar pure component spectral responses into clusters; determining a representative spectral response for each cluster; and correlating the representative spectral response for each cluster with one of the molecular species.

In a further implementation consistent with the present invention, an apparatus includes a light separator, a spectral array detector, and a processor. The light separator spatially separates wavelengths of light representing multiple spectrally-distinguishable molecular species. The spectral array detector generates data relating to intensity as a function of the wavelengths separated by the light separator. The processor collects the data from the spectral array detector, creates a data matrix from the collected data, each element in the data matrix representing a signal intensity at a particular time and over a particular range of light wavelengths or an approximated time-derivative of the signal intensity, identifies regions in the data matrix having spectral response characteristics of at least one of the molecular species, determines a set of pure component spectral responses from the identified regions, groups similar pure component spectral responses into clusters, determines a representative spectral response for each cluster, and correlates the representative spectral response for each cluster with one of the molecular species.

In yet another implementation consistent with the present invention, a system performs spectral calibration. The system collects data from monitoring an analytical separation of multiple spectrally-distinguishable molecular species and creates a data matrix from the collected data. Each element in the data matrix represents a signal intensity at a particular time and over a particular range of light wavelengths or an approximated time-derivative of the signal intensity. The system then identifies binary mixture regions within the data matrix, determines pairs of the binary mixture regions that contain one common spectral response, identifies a component that represents the one common spectral response using data in the determined pairs, groups the one common spectral response from each of the determined pairs into clusters, determines a representative spectral response for each cluster, and correlates the representative spectral response for each cluster with one of the molecular species.

In another implementation consistent with the present invention, a computer-readable medium stores instructions executable by a processor for performing a spectral calibration method. The method includes collecting data from monitoring an analytical separation of multiple spectrally-distinguishable molecular species; creating a data matrix from the collected data, each element in the data matrix representing a signal intensity at a particular time and over a particular range of light wavelengths or an approximated time-derivative of the signal intensity; identifying binary mixture regions within the data matrix; determining pairs of the binary mixture regions that contain one common spectral response; identifying a component that represents the one common spectral response using data in the determined pairs; grouping the one common spectral response from each of the determined pairs into clusters; determining a representative spectral response for each cluster; and correlating the representative spectral response for each cluster with one of the molecular species.

In yet another implementation consistent with the present invention, an apparatus includes a light separator, a spectral array detector, and a processor. The light separator spatially separates wavelengths of light representing multiple spectrally-distinguishable molecular species. The spectral array detector generates data relating to intensity as a function of the wavelengths separated by the light separator. The processor collects data from monitoring an analytical separation of multiple spectrally-distinguishable molecular species, creates a data matrix from the collected data, each element in the data matrix representing a signal intensity at a particular time and over a particular range of light wavelengths or an approximated time-derivative of the signal intensity, identifies binary mixture regions within the data matrix, determines pairs of the binary mixture regions that contain one common spectral response, identifies a component that represents the one common spectral response using data in the determined pairs, groups the one common spectral response from each of the determined pairs into clusters, determines a representative spectral response for each cluster, and correlates the representative spectral response for each cluster with one of the molecular species.

BRIEF DESCRIPTION OF THE DRAWINGS

The accompanying drawings, which are incorporated in and constitute a part of this specification, illustrate an embodiment of the invention and, together with the description, explain the invention. In the drawings.

DETAILED DESCRIPTION

The following detailed description of the invention refers to the accompanying drawings. The same reference numbers in different drawings identify the same or similar elements. Also, the following detailed description does not limit the invention. Instead, the scope of the invention is defined by the appended claims and equivalents.

Systems and methods consistent with the present invention perform spectral calibration for spectrally-distinguishable molecular species.

EXEMPLARY SYSTEM

Figure 1:
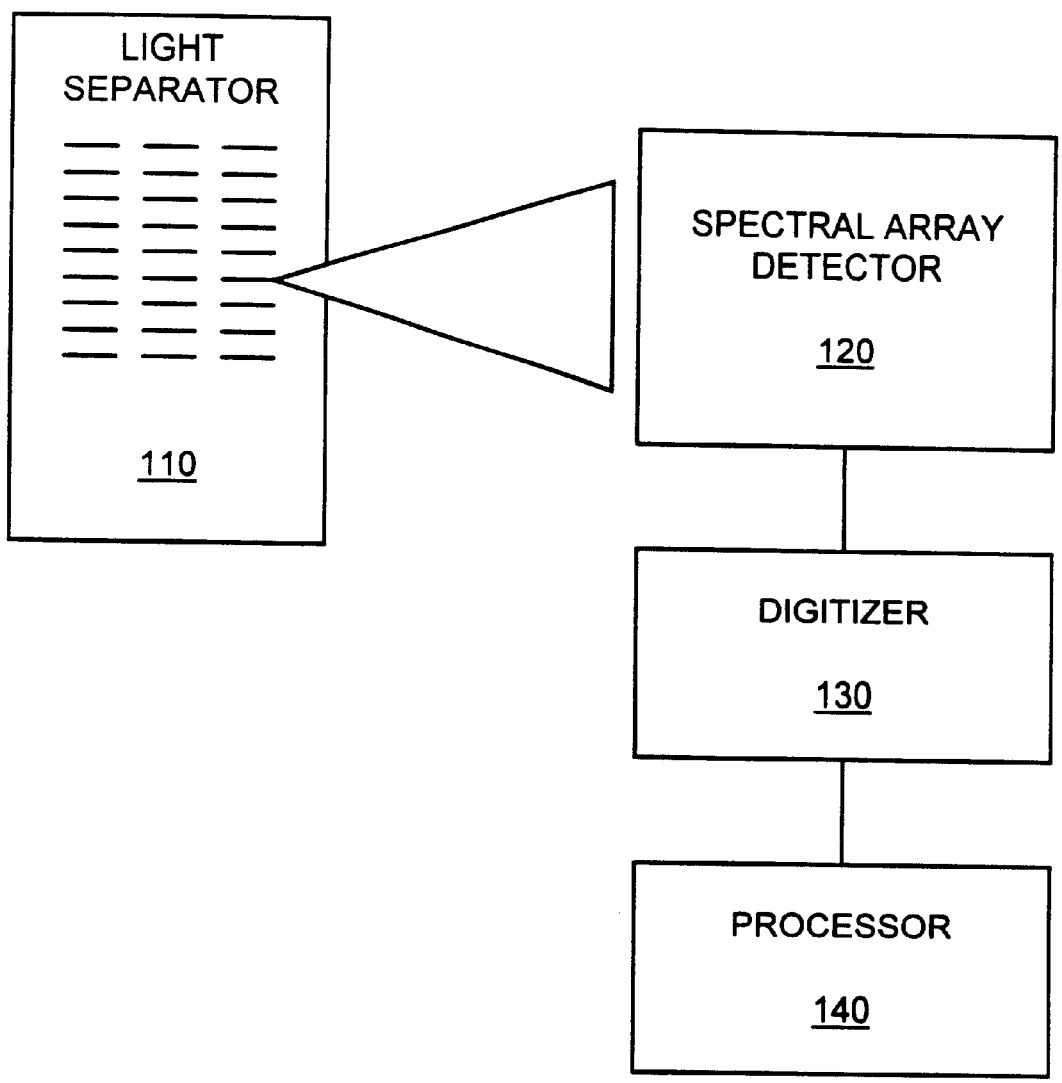
FIG. 1 is a diagram of an exemplary system consistent with the present invention.

FIG. 1 is an exemplary system 100 consistent with the present invention. The system 100 includes a light separator 110, a spectral array detector 120, a digitizer 130, and a processor 140. The light separator 110 spatially separates multiple spectrally-distinguishable species. The light separator 110 may include a spectrograph, a diffraction grating, a prism, a beam splitter in combination with optical filters, or similar elements.

Figure 2:
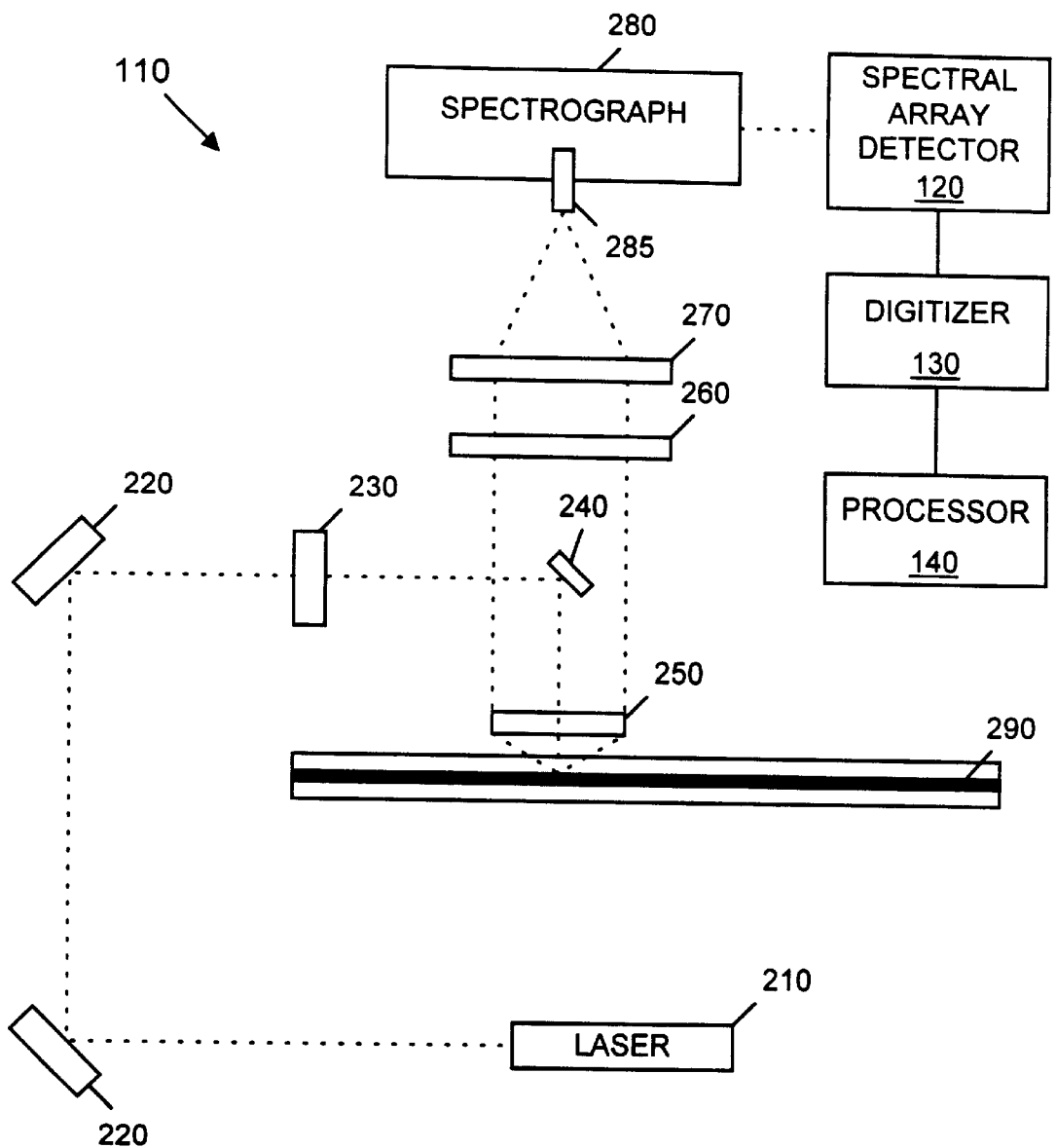
FIG. 2 is a detailed diagram of the light separator of FIG. 1 in an implementation consistent with the present invention.

FIG. 2 is a detailed diagram of the light separator 110 in an implementation consistent with the present invention. The light separator 110 includes a laser 210, a pair of mirrors 220, lenses 230, mirror 240, lens 250, filter 260, lens 270, and spectrograph 280. The laser 210 is an excitation light source, such as an argon ion laser, that may emit a polarized light beam. The mirrors 220 may be adjustably mounted to direct the laser light beam to the desired location. The lenses 230 may include telescope lenses that reduce the diameter of the light beam reflected by the mirrors 220 and present the reduced light beam to the mirror 240. The mirror 240 may include a bending mirror that directs the light to an electrophoresis medium 290, such as an aqueous gel.

The lens 250 may include an aspheric collection lens that collects the light emitted from the laser-excited medium 290 and collimates the light in the direction of the filter 260, bypassing mirror 240. The filter 260 may include a laser rejection filter that reduces the level of scattered laser light transmitted to the lens 270. The lens 270 may include a plano-convex lens that focuses the filtered light to the spectrograph 280. The spectrograph 280 may include a slit 285 that receives the light from the lens 270 and a blaze grating (not shown) that separates the light into its spectral components. The spectrograph 280 outputs the light to the spectral array detector 120.

Returning to FIG. 1, the spectral array detector 120 includes an optical detector that can simultaneously detect and identify an intensity of multiple wavelengths of light. The spectral array detector 120 may include an array of detector elements sensitive to light radiation, such as a diode array, a charged coupled device (CCD), a charge induction device (CID), an array of photomultiplier tubes, etc. The output of the spectral array detector 120 is light intensity as a function of array location, such that the array location can be directly related to the wavelength of the light impinging on that location.

The digitizer 130 receives the output from the spectral array detector 120, digitizes it, and presents it to the processor 140. The digitizer 130 may include an analog-to-digital converter or a similar device. The processor 140 operates upon the digitized output of the spectral array detector 120 to perform spectral calibration. The processor 140 may include any conventional processor, microprocessor, digital signal processor, or computer capable of executing instructions. The processor 140 may also include memory devices, such as a RAM or another dynamic storage device, a ROM or another type of static storage device, and/or some type of magnetic or optical recording medium and its corresponding drive; input devices, such as a keyboard and a mouse; output devices, such as a monitor and a printer; and communication device (s) to permit communication with other devices and systems over any communication medium.

As will be described in detail below, the processor 140, consistent with the present invention, operates upon data resulting from an analytical separation of spectrally-distinguishable molecular species to perform spectral calibration. The processor 140 performs the spectral calibration by executing sequences of instructions contained in a memory. Such instructions may be read into the memory from another computer-readable medium or from another device over a communications medium. Execution of the sequences of instructions contained in the memory causes the processor 140 to perform the methods that will be described hereafter. Alternatively, hardwired circuitry may be used in place of or in combination with software instructions to implement the present invention. Thus, the present invention is not limited to any specific combination of hardware circuitry and software.

EXEMPLARY SPECTRAL CALIBRATION PROCESSING

The processor 140 uses the data from the spectral array detector 120 to generate an electropherogram Y, with a dimension of $n_t \times n_b$, which is a matrix of intensity as a function of spectral bin number (ranging from 1 to $n_b$) and time of detection (ranging from 1 to $n_t$). The column vectors of the electropherogram are composed of intensity values for a given detector element, or a sum of intensity values over a series of detector elements, at different times, and the row vectors are composed of intensity values for a given time measured at different detector elements or a sum of intensity values measured over a series of detector elements. The method used to identify regions in the electropherogram Y that have a spectral response characteristic of one or two spectrally-distinguishable molecular species depends on the type of data that is expected.

If the data includes regions of pure component spectral responses, a Type I method may be used. This type of data would be expected in situations in which the analytical separation process results in at least one isolated peak representing each of the distinct pure-component molecular species, such as a DNA fragment, labeled with a different one of the dyes. The Type I data need not, however, consist entirely of isolated pure components, but may also contain regions of mixtures (i.e., spatially-indistinguishable peaks).

Alternatively, if the data does not include such regions, but includes regions of binary component spectral responses, then a Type II method may be used. This type of data would be expected in situations in which the analytical separation process is unable to provide spatially-distinguished peaks in which each peak consists of a pure component molecular species, and can only provide regions resulting from the combined emission from two dyes (i.e., a binary mixture region). Typically, as in DNA sequencing applications, the peaks constituting the separate components of the mixture are out-of-phase to some extent in the time domain of the electropherogram. The Type II data may also be characterized by some regions of isolated (pure) components, but in such a way that it is difficult to reliably distinguish between these and other (similar) regions containing low levels of "contamination" from another species.

Both methods consistent with the present invention are methods of Factor Analysis (FA) or Blind Separation of Sources (BSS). Each method operates well with particular types of data. The goal of both, however, is the same; namely, to extract the source or basis functions representing the independent components present in a mixture without any specific prior knowledge of their shape (hence "blind" in BSS). In the present context, the physical components include distinct dyes and the basis functions include their individual fluorescence spectra, such as relative emission intensity versus wavelength.

Another term that is frequently encountered in this context is mixture analysis (i.e., the output signals are produced by an instantaneous linear mixture of the source signals). As general methodologies, FA and/or BSS have been applied in many different contexts, including gas chromatography, mass spectrometry, magnetic resonance spectroscopy, as well as other more distantly-related applications in signal processing and statistical analysis.

The methods consistent with the present invention are deterministic in the sense that they are designed to isolate and classify regions that are anticipated to always occur in the two types of electropherogram signals considered. Given that the requisite regions are found, the subsequent solution for the unknown factor vectors can be shown to be optimal (for example, in a least mean-squares sense). Should the regions not be found, the method fails to produce a result in favor of generating an erroneous or inaccurate one. In this regard, the methods are different from classical FA or BSS that typically optimize based on general (e.g., statistical) principles that may or may not be truly characteristic of the signals being analyzed in the present context.

A. Type I Method

Generally, the Type I method employs a strategy of locating regions that have spectral response characteristics of at least one of spectrally-distinguishable molecular species, examining all of the regions to identify a set of pure component spectral responses, and grouping similar pure component spectral responses into clusters. The method selects a representative spectral response for each cluster and correlates the representative spectral response for each cluster with one of the molecular species.

Figure 3:
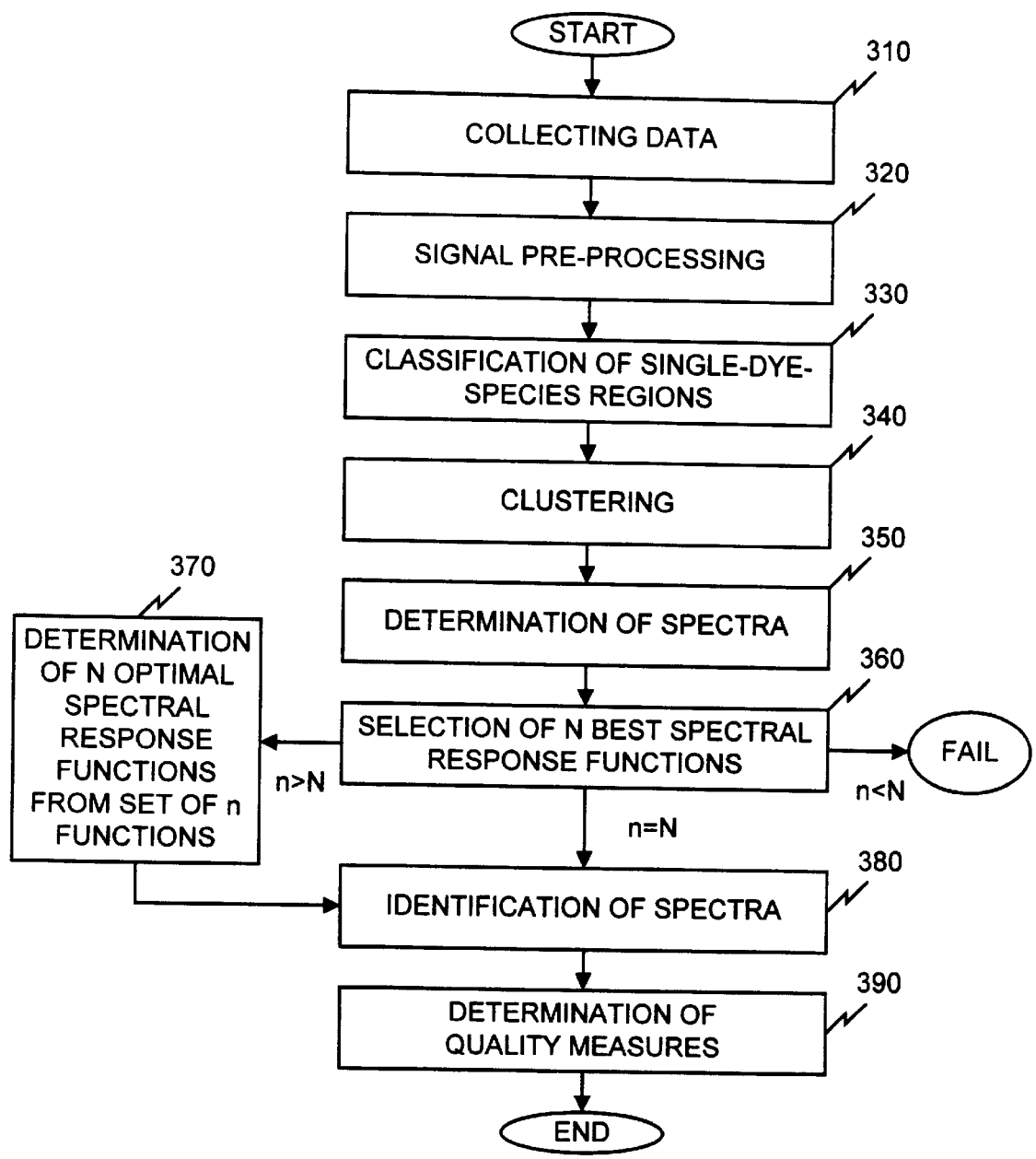
FIG. 3 is a flowchart of Type I processing consistent with the present invention.

FIG. 3 is a flowchart of Type I processing consistent with the present invention. Type I processing begins with the processor 140 collecting data from the spectral array detector 120 [step 310]. The processor 140 uses the collected data to generate an electropherogram Y that contains intensity data representing fragments, such as DNA fragments, of different sizes labeled by one or more dye species.

The Type I method assumes that at least one peak representing each of the N dyes is well separated in the time domain of the electropherogram Y from any peaks representing any of the other dyes. The electropherogram may contain systematic flaws due to baseline drift (i.e., a non-stationary background), spikes caused by spurious fluorescent events, regions of multiple dye signals, and regions of saturation.

Figure 4:
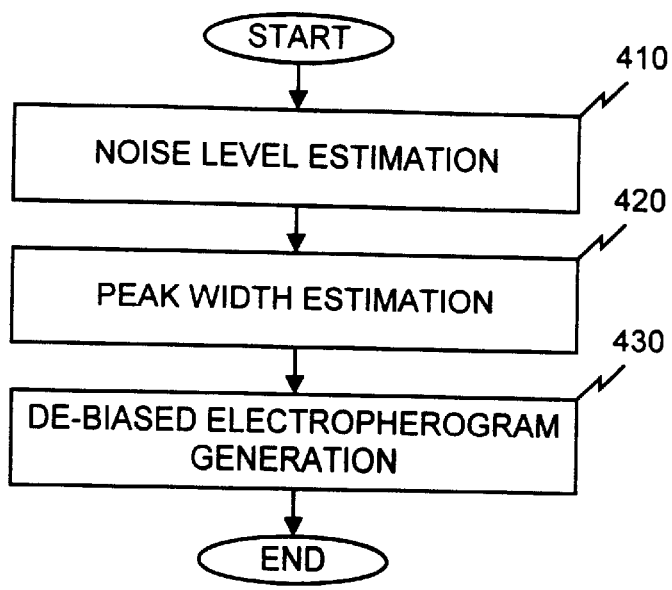
FIG. 4 is an exemplary flowchart of the signal pre-processing of FIG. 3.

The processor 140 then performs signal pre-processing [step 320]. FIG. 4 is a flowchart of signal pre-processing consistent with the present invention. When performing signal pre-processing, the processor 140 may estimate the noise level in each spectral bin number (see Appendix A.1) [step 410] and the typical width of a peak representing one of the dye-labeled components using a conventional peak width estimation technique (see Appendix A.2) [step 420]. The processor 140 then generates a de-biased electropherogram Z, of size $[n_t \times n_b]$, from the electropherogram Y [step 430]. The processor 140 may do this through estimation of the baseline and subtraction from Y (see Appendix A.3); through subtraction, such that $Z(i,:)=Y(i,:)-Y(i-\delta,:)$, where ":" refers to all elements in a row or column of a matrix, and $\delta$ is the lag chosen based on a characteristic peak-width scale; or through a smooth derivative of Y, using, for example, a Savitsky-Golay filter, as described in William H. Press et al., "Numerical Recipes in C," The Art of Scientific Computing, 2nd Ed., pp. 650–655, 1995.

Figure 5:
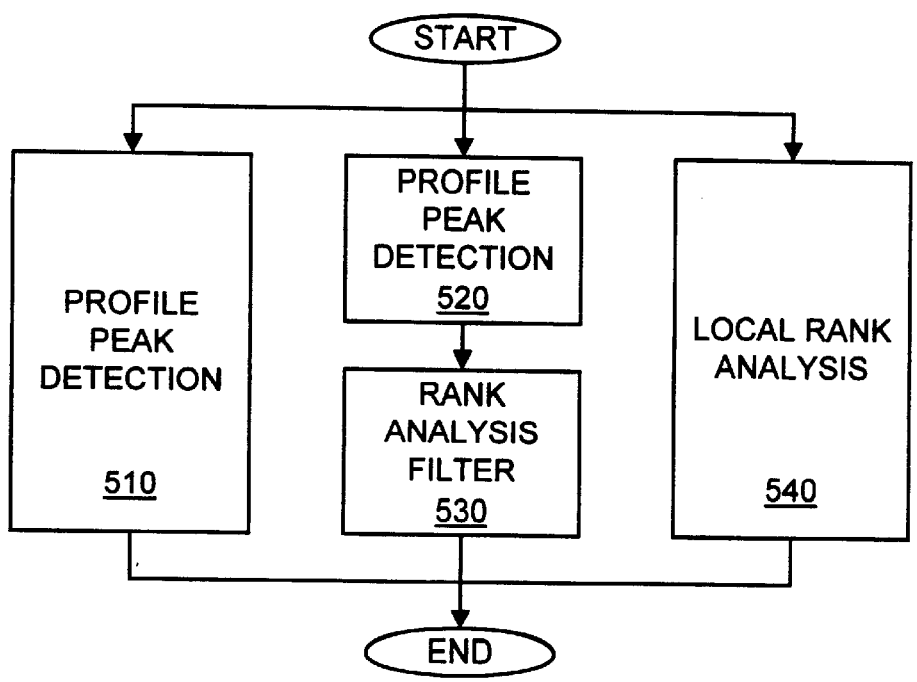
FIG. 5 is an exemplary flowchart of the classification of single-dye-species regions of FIG. 3.

Returning to FIG. 3, the processor 140 classifies the single-dye-species regions [step 330]. FIG. 5 is a flowchart of processing for classifying single-dye-species regions in a manner consistent with the present invention. The processor 140 classifies the species regions by performing: profile peak detection [step 510]; profile peak detection [step 520] and rank analysis filtering [step 530]; or local rank analysis [step 540].

In step 510, the processor 140 determines a profile equal to the sum of intensity values across spectral bins at each time slice. This results in an $[n_t \times 1]$ electropherogram. The processor 140 then detects peaks in the profile by locating inflection points in the profile or by using other peak detection methods (see Appendix A.4). The processor 140 keeps only those peaks that pass some heuristic requirements, such as those having a width greater than some minimum (to remove fluorescent spikes) or having a height greater than some threshold, for example, based on a signal-to-noise minimum or using the previous noise estimation.

The processor 140 assumes that the remaining peaks represent single dye-labeled fragments and selects a region of time slices around each remaining peak possibly based on user input or the previous peak width estimation. The concatenation of regions around each selected peak forms the set r of points (described below). For example, if the processor 140 selects four peaks at $t=\{100,200,300,400)\}$, and if one additional point on either side of each peak is used, then $\tau=\{99,100,101,199,200,201, \ldots ,401\}$.

In step 520, the processor 140 performs the same profile peak detection described with regard to step 510. In step 530, the processor 140 estimates, for each peak i detected, the rank of the matrix formed from the data $z_i$ in a region centered in time around the peak position $t_i$. For example, $r_i=\{t_i-\delta,t_i-\delta+1, \ldots ,t_i, \ldots ,t_i+\delta\}$, and $z_i=Z(r_i,:)$. In this context, the rank provides an estimate of the number of pure factors (in this case, dye spectra) present in the data in that region. The processor 140 determines the singular values of $z_i$ using a conventional process for solving a linear system of equations, such as Singular Value Decomposition (SVD) described in William H. Press et al., "Numerical Recipes in C," The Art of Scientific Computing, Second Ed., pp. 59–70, 1995. The processor 140 may use a heuristic on singular values to estimate rank (see Appendix A.5). Alternatively, the processor 140 may sort from largest to smallest values, find the last singular value in the sorted list that is above a predefined cutoff, and set its index equal to the rank.

The processor 140 selects peaks that pass the rank analysis with a rank equal to one. The processor 140 then selects a region of time slices around each selected peak, where, again, the concatenation of regions around each selected peak forms the set τ of points.

In step 540, the processor 140 determines a rank, for each time t, of Z by using a data matrix in a region r(t) around each time slice t. The processor 140 estimates the rank of the matrix formed from the data $z_i$ in a region centered in time around the time slice $t_i$. For example, $r_i=\{t_i-\delta, t_i-\delta+1, \ldots, t_i+\delta\}$, and $z_i=Z(r_i,:)$. In this context, the rank provides an estimate of the number of pure factors (in this case, dye spectra) present in the data in that region. The processor 140 determines the singular values of $z_i$ using, for example, SVD. The processor 140 may use a heuristic on singular values to estimate rank. Alternatively, the processor 140 may sort from largest to smallest values, find the last singular value in the sorted list that is above a predefined cutoff, and set its index equal to the rank. The processor 140 then selects points or regions that pass rank analysis with a rank equal to one. This defines a set τ of time slices.

From steps 510–540, the processor 140 obtains a set τ of indices into the de-biased data Z. The processor 140 assumes that each time slice in this set represents the response from a single dye. This may be represented as:

$$Z(\tau_i, j) = a(\tau_i) \times f_c(j),$$

where the index j runs from 1 to $n_b$ (i.e., the number of spectral bins), $a(\tau_i)$ is an arbitrary amplitude, and $f_c$ is the response function for a specific, but unknown, dye. The set τ is assumed at this point to contain such representatives from each of the N dyes.

Returning to FIG. 3, the processor 140 clusters the same dye species [step 340]. The goal of the clustering is to separate the set τ into n groups or subsets of vectors, labeled as $\{\tau^{(1)}, \tau^{(2)}, \ldots, \tau^{(n)}\}$. Each subset $\tau^{(k)}$ consists of indices that point to regions (rows) of the electropherogram representative of like spectral response. In one implementation consistent with the present invention, the processor 140 pre-selects the number of clusters n to be the same as the number of expected dye-labeled components N.

In another implementation consistent with the present invention, the processor 140 performs an algorithm that automatically selects the number of clusters that best suits the input data. In this way, the processor 140 may subsequently classify the data in each cluster k as representing: (1) a pure-dye response, (2) a noise region that erroneously passed the selection process, or (3) a mixed-dye response that appeared as a pure-dye response because of a high degree of peak overlap. In this implementation, the present invention guards against situations where the input data is flawed, for instance due to failed chemistry reactions, failed electrophoresis injection, off-scale data from the detector, etc.

To perform the cluster analysis, the processor 140 defines a distance measure between two distinct response functions, which can be represented as vectors in the $n_b$-dimensional space and are equivalent to rows of the de-biased electropherogram. For example, in one implementation, the distance measure is the generalized angle between the two vectors. The processor 140 may then use one of several available methods for clustering, including hierarchical and partitional methods (see, e.g., A. K. Jain et al., "Data Clustering: A Review," ACM Inc., (date unknown)). In the former case, the processor 140 will typically compute the pair-wise distance between each unique pair of vectors labeled by the set τ, thus defining a similarity matrix on the input data. Then, for example, linkage analysis in conjunction with some rule or threshold on the linkage distances may be used to determine the set (and number) of clusters.

For the applications discussed here, a partitional clustering approach may be used because the data are generally expected to form tight and well-separated clusters. In this case, the processor 140 performs a single-pass agglomerative process that naturally chooses the number of clusters n. This algorithm is time-efficient and relies on a single tuneable parameter that determines the proximity threshold for defining a new cluster, given the computation of distance between a trial vector and each of a set of defined cluster "centroids." The threshold parameter relates to the amount of variation anticipated among clean, same-dye responses in the data set. The processor 140 may implement the following algorithm:

(i) For each element of the set τ, define a vector $\vec{z}^{(i)} = Z(\tau_i, 1:n_b)$.

(ii) Normalize each $\vec{z}^{(i)}$ to unit length: $\vec{z}^{(i)} \leftarrow \vec{z}^{(i)} / \sqrt{\vec{z}^{(i)} \cdot \vec{z}^{(i)}}$.

(iii) Initialize to n=1 and define the "centroid" of the first cluster to be the vector $\vec{c}^{(1)} = \vec{z}^{(1)}$. Initialize a counter k to k>1.

(iv) Set k=k+1. If k>number of elements in τ, the algorithm stops.

(v) Compute the angle $\alpha_j = \cos^{-1}(\vec{z}^{(k)} \cdot \vec{c}^{(j)})$ for each of the existing clusters j={1:n}. Choose the cluster ĵ for which this angle is the smallest.

(vi) If $\alpha_j < \alpha_0$, where $\alpha_0$ is an ad hoc cutoff parameter for the algorithm, then add the point k to the cluster ĵ. Re-compute the centroid of the ĵ cluster as the mean or median of the current members. Go to step (iv).

(vii) Otherwise, increment the number of clusters, n→n+1. Define the centroid of the new cluster to be $\vec{c}^{(n)} = \vec{z}^{(k)}$. Go to step (iv).

With a set of n clusters defined, the processor 140 computes a single response function that is representative of the data in each cluster [step 350]. If n<N, the calibration aborts at this point, since the expected number of spectra have not been found. Otherwise, with n≧N, the processor 140 determines the representative response functions using one of several possible methods. For example, the processor may compute the point-wise mean or weighted mean (e.g., based on the cumulative signal intensity of each measurement) of the vectors within each cluster. Alternatively, to improve robustness, the processor 140 may compute a median response vector, a mean or weighted mean of some subset of each cluster that represents a controlled amount of variation, etc.

In the preferred method for step 350, however, the processor 140 performs a reduction-of-dimension on the data in each cluster using Principle Component Analysis (PCA), described in A. Hyvarinen, "Survey on Independent Component Analysis," Neural Computing Surveys, 2:94–128, 1999. Since the number of true components represented in each cluster is expected to be one, the first principle component defines the target response function. The processor 140 may implement the PCA using, for example, the Singular Value Decomposition (SVD) algorithm, as described in William H. Press et al., "Numerical Recipes in C," The Art of Scientific Computing, 2nd Ed., pp. 59–70, 1995. Specifically, for each cluster k, the processor 140 defines the matrix $Z^{(k)}=Z(\tau^{(k)},1:n_b)$, computes the SVD on the matrix, and defines the first output direction vector as the response function $f_k$.

After determining the response functions, the processor 140 selects the N best spectral response functions [step 360]. For error prevention, the processor may impose ad hoc limitations on the shape of the candidate response functions and eliminate those that do not pass from the candidate set. For example, the processor 140 may require the percentage of negative area in the integral of $f_k$ to be below a threshold value (response functions are expected to be positive), or it may require that the first moment of the response functions be below some pre-established maximum value (true response functions are expected to be peaked around some wavelength region, and spurious fluorescence or detection noise can produce very flat response functions with a large moment). The processor 140 then re-computes n to reflect any rejected response functions. Although the use of these sorts of criteria amounts in principle to the introduction of "prior knowledge" into the source separation problem, heuristic methods such as these can typically be formulated broadly enough to accommodate the requisite range of solution vectors.

With heuristic filtering completed, the processor 140 in step 360 examines the new number n of candidate response functions. If n<N, the processor 140 aborts the calibration procedure. If n=N, the processor 140 proceeds to step 380. If n>N, the processor 140 may either (1) abort the calibration, or (2) proceed to step 370. In step 370, (n–N) candidate response functions are presumed to originate from regions in the data where two dye-labeled components overlapped "in phase" in the electropherogram and, therefore, appeared erroneously as a pure component region to the single-dye-region classifier, step 330. The processor 140 determines the optimal subset of N response functions from which the remaining (n–N) can be formed using a positive superposition of binary states. For a detailed explanation, see Appendix A.6. The processor 140 then filters out the incorrect candidates and proceeds to step 380.

Figure 6:
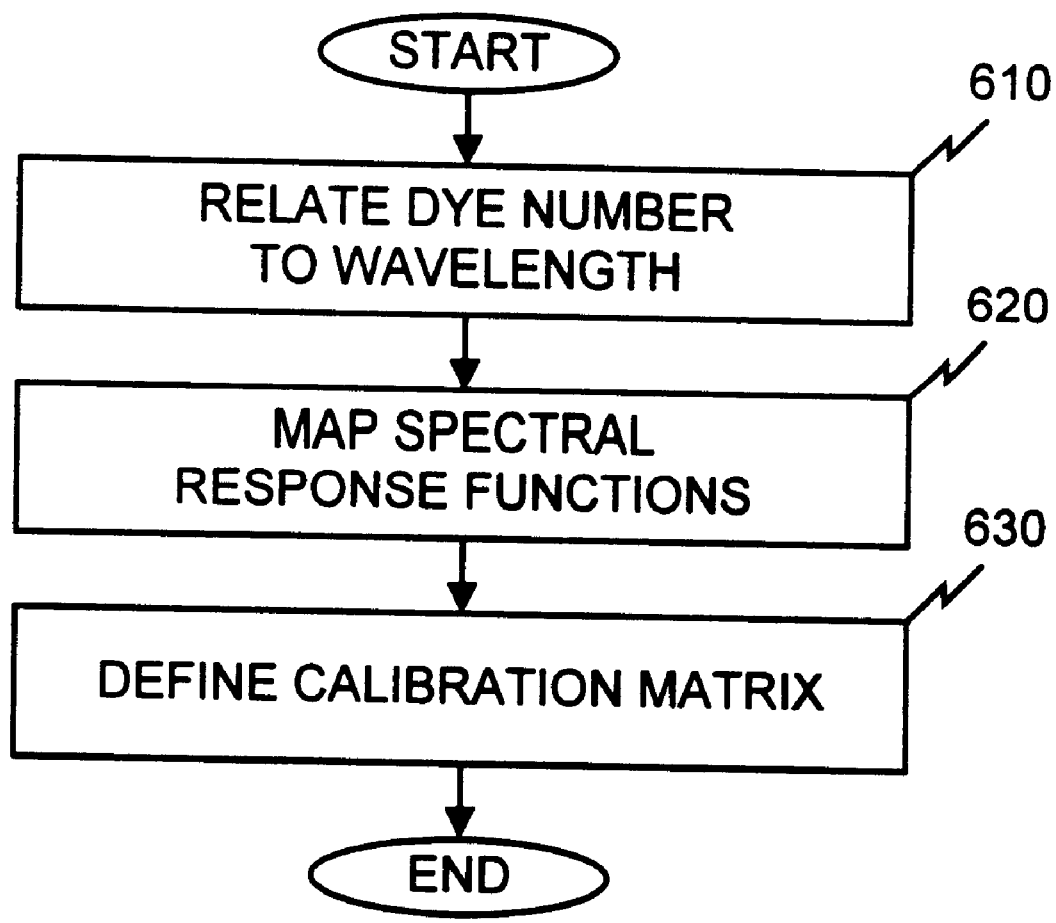
FIG. 6 is an exemplary flowchart of the identification of spectra of FIG. 3.

In step 380, the processor 140 identifies the spectra by mapping response functions to dye numbers. FIG. 6 is a flowchart of exemplary processing for identifying spectra in a manner consistent with the present invention. The processor 140 uses an established convention relating the dye number to the wavelength order of maximum emission [step 610]. For example, four dyes are numbered 1 through 4 corresponding to the dye which emits most in the blue (shortest wavelength) through the dye that emits most in the red (longest wavelength).

The processor 140 then maps from the N spectral response functions $f_i$, where now i={1, . . . , N}, to dye numbers {1, . . . , N} using a scalar-valued function $\lambda=F(f)$ that maps each response function $f_i$ to an approximate bin number $\lambda_i$ of maximum emission [step 620]. For example, $F(f)$ may represent the center-of-mass of $f$ or the location of the maximum of $f$.

The processor 140 normalizes the spectral $f_i(j)$ based on a previously established convention, such as max$[f_i(j)]\equiv 1$. The processor 140 then defines the calibration matrix C [step 630]. The matrix C includes the reordered row vectors $f_i$, where now i={1, . . . , N} corresponds to dyes 1 through N as described above. Specifically, $C_{ij}=f_i(j)$. This is the calibration output of the processor 140 for Type I processing. The calibration matrix is equivalent to what is conventionally known as the mixing matrix in BSS.

Optionally, at this point, the processor 140 may determine quality measures, such as for error detection [step 390] (FIG. 3). The processor 140 defines a multicomponent matrix M as the pseudo-inverse of matrix C. In the case where the number of spectral bins is the same as the number of dyes ($n_b$=N), M is the ordinary matrix inverse of C. In this case, M has dimensions of [$n_b$×N]. The processor 140 may use matrix multiplication to convert the $n_t$×$n_b$ raw data matrix Y to the $n_t$×N relative-dye-intensity matrix $Y_M$, such that $Y_M$=Y×M.

The processor 140 may determine the heuristic quality measure using $Y_M$. For example, there may be a self-consistency check by which the processor 140 checks for PU/PD in alternate dye channels under presumed pure dye peaks. The processor 140 may do this by performing a second derivative ratio test of alternate dye channels around presumed pure dye peaks. The processor 140 may also determine the condition number of the matrix C and compare it to its expected range based on prior knowledge of the target dye set spectra.

B. Type II Method

Generally, the Type II method employs a strategy of (1) locating all binary mixture regions (BMRs); (2) examining all pairs of BMRs and determining which of the pairs share one and only one common dye (e.g., [U1,U2]+[U1,U3]), where U stands for "unknown;" and (3) for each such pair, extracting the spectrum for the common factor using an optimization technique (described below). The sample data is assumed to be rich enough in BMR pair combinations so as to provide at least one example of each of the unknown spectra by using a binary-mixture pairing approach. In other words, it is assumed that each dye forms a clean binary region with at least two other dyes. This naturally puts a lower limit on the number of dyes in the mixture (3) for the Type II method to apply.

The extracted spectra are grouped into same-dye sets using cluster analysis. Finally, a best "mean" spectrum is computed for each cluster; the optimal set of spectra to represent the target dye set is selected; and the correspondence between the unknowns and the target dyes is established based on a wavelength ordering criterion.

Figure 7:
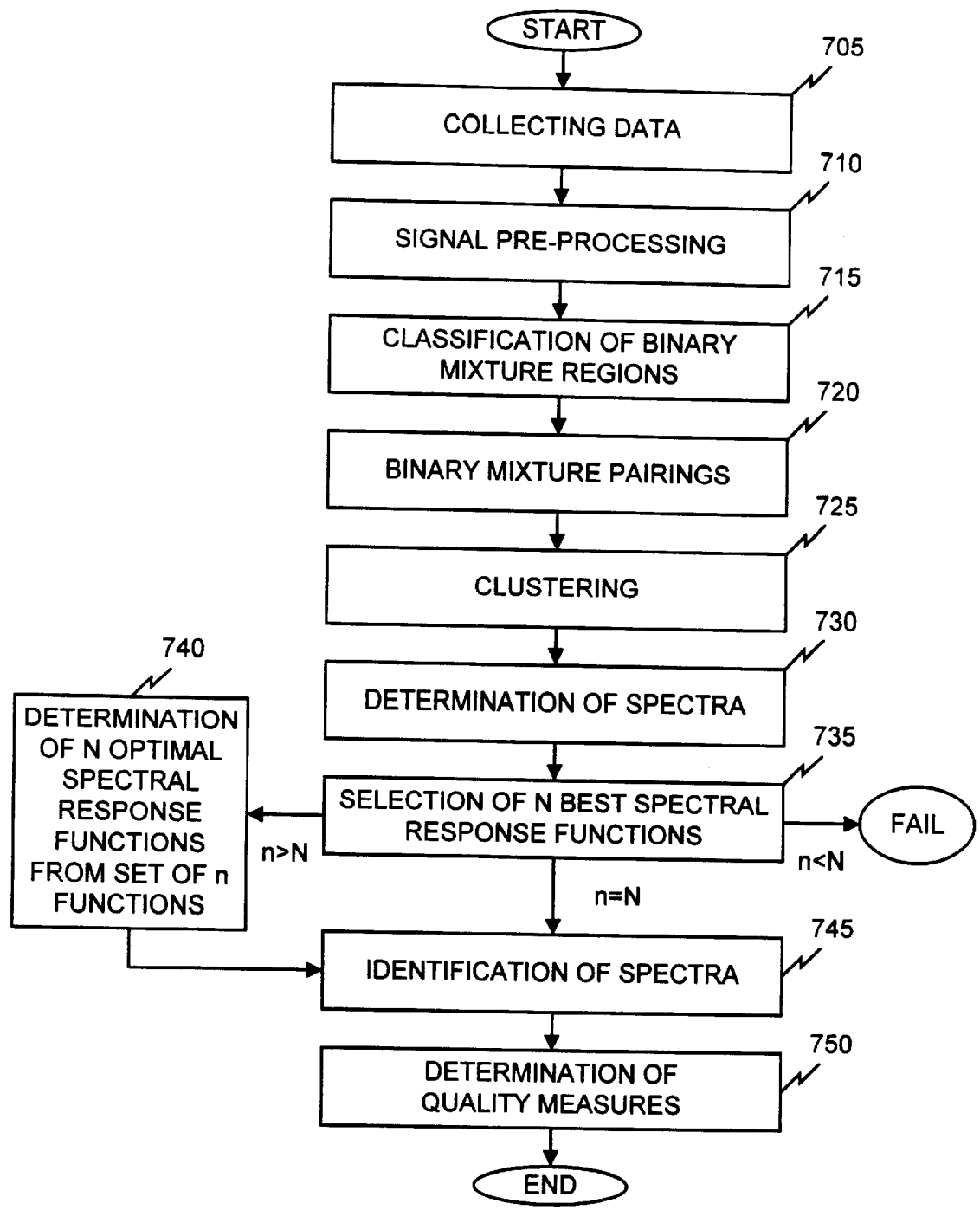
FIG. 7 is a flowchart of Type II processing consistent with the present invention.

FIG. 7 is a flowchart of Type II processing consistent with the present invention. Type II processing begins with the processor 140 collecting data from the spectral array detector 120 [step 705]. The processor 140 uses the collected data to generate an electropherogram Y that, in this case, contains fluorescence intensity data resulting from electrophoresis, detection of combined reactions, such as 4-color sequencing reactions, and a primer or terminator. The electropherogram may contain systematic flaws due to baseline drift (i.e., a non-stationary background), spikes caused by spurious fluorescent events, and regions of saturation.

The processor 140 then performs signal pre-processing [step 710], similar to that described with regard to FIG. 4. The processor 140 estimates the noise level in each spectral bin number and the typical width of a peak representing one of the dye-labeled components. The processor 140 then locates a starting point and generates a de-biased electropherogram Z from the electropherogram Y. The processor 140 may do this through estimation of the baseline and subtraction from Y; through subtraction, such that Z(i,:)=Y(i,:)−Y(i−δ,:), where δ is the lag chosen based on a characteristic peak-width scale; or through a smooth derivative of Y, using, for example, a Savitsky-Golay filter. For performance optimization, the processor 140 may downsample Y in the spectral bin dimension (assuming that the number of bins $n_b$ is larger than the number of dyes $n_{dye}$) and/or the time dimension.

The processor 140 classifies the BMRs [step 715]. To classify them, the processor 140 determines a rank, for each time t, of Z by using a data matrix in a region r(t) around each time slice t. The processor 140 estimates the rank of the matrix formed from the data $z_i$ in a region centered in time around the time slice $t_i$. For example, $r_i=\{t_i-\delta, t_i-\delta+1, \ldots, t_i, \ldots, t_i30\ \delta\}$, and $z_i=Z(r_i,:)$. In this context, the rank provides an estimate of the number of pure factors present in the data in that region. The processor 140 determines the singular values of $z_i$ using, for example, SVD. The processor 140 may use a heuristic on singular values to estimate rank. Alternatively, the processor 140 may sort from largest to smallest values, find the last singular value in the sorted list that is above a predefined cutoff, and set its index equal to the rank.

The processor 140 then selects contiguous regions greater than a predetermined minimum length that passes rank analysis with a rank equal to two. For the following discussion, assume that each time slice of each BMR represents the response from some unknown mixture of two as yet unknown dyes. These regions are denoted by $R_i$, where the index i runs from 1 to the number of regions $N_r$ found in the data, and each region consists of a set of contiguous time slices, $R_i = \{t_1^{(i)} : t_{n_i}^{(i)}\}$.

The processor 140 constructs a set of $N_R (N_R-1)/2$ unique pairings of BMRs, where each pair in the set can be denoted $[R_i, R_j]$, where i runs from 1 to $N_R$, j runs from 1 to i-1. To determine a single-dye spectra from the set [step 720], the processor 140:

(i) determines the rank over the combined region of time slices, $\{t_1^{(i)} : t_{n_i}^{(i)}, t_1^{(j)} : t_{n_j}^{(j)}\}$;

(ii) if the rank is three, extracts the common factor $\vec{f}^{(ij)}$ using, for example, the method described in Appendix B, and records this vector in a list of extracted pure-dye spectra; and (iii) using the next $[R_i, R_j]$ pair, repeats step (i). If there are no more pairs to process, processing proceeds to step 725.

In step 725, the processor 140 clusters same-dye-species spectra. For the purposes of this discussion, it is assumed that the complete list of pure-dye spectra computed in step 720 is labeled by a single index as $\vec{f}^{(k)}$. As for Type-I processing, each $\vec{f}^{(k)}$ is an $n_b$-vector, where $n_b$ is the number of virtual filters in the collected data. The processor 140 separates the set into n clusters, where each cluster contains one or more independently-computed spectra $\vec{f}^{(k)}$ belonging to the same dye.

The steps of:

[725] Clustering of same-species response functions;

[730] Determination of representative response functions for each cluster;

[735] Selection of the N (number of expected dyes) best response functions;

[740] Determination of N optimal functions when n (number of clusters)>N; and

[745] Identification of spectra are identical to the final stages of processing for the Type-I data, as described in Subsection A above for steps 340, 350, 360, 370 and 380 respectively. The only distinction is that in the Type-II case, the initial set of candidate spectral functions (the $\vec{f}^{(k)}$) that constitute the input to these five steps have been derived mathematically from a higher-level classification/optimization process [steps 715–720].

By contrast, in the Type-I case, the set $\vec{f}^{(k)}$ are drawn directly from the de-biased electropherogram, where the processor 140 has indicated the presence of single-component responses. In addition, to mirror the Type-I processing, the individual unit-norm direction vectors that constitute the clusters for Type-II (output of step 725) may be weighted by some measure of the signal intensity representative of the data in the regions used to compute each vector. This practice would constitute a minor variation in the determination of representative responses for the clusters for the Type-II processing in step 730 as opposed to the Type-I processing in step 350.

Therefore, with the completion of step 745, the processor 140 proceeds to step 750, the optional determination of quality measures. Identically to the Type-I processing carried out in step 390, the processor 140 may compute the condition number of the calibration matrix C and compare it to an expected range based on prior knowledge of the target dye-set spectra. And, similarly to the Type-I case, the processor 140 may compute a quality measure using the multicomponented data $Y_M = Y \times M$, by performing a self-consistency check on the magnitude of PU/PD in regions of known binary mixtures. Here, there is a slight variation from the Type-I processing in that the PU/PD level can be estimated only from the two "empty" dye channels of each BMR.

EXAMPLES

Figure 8:
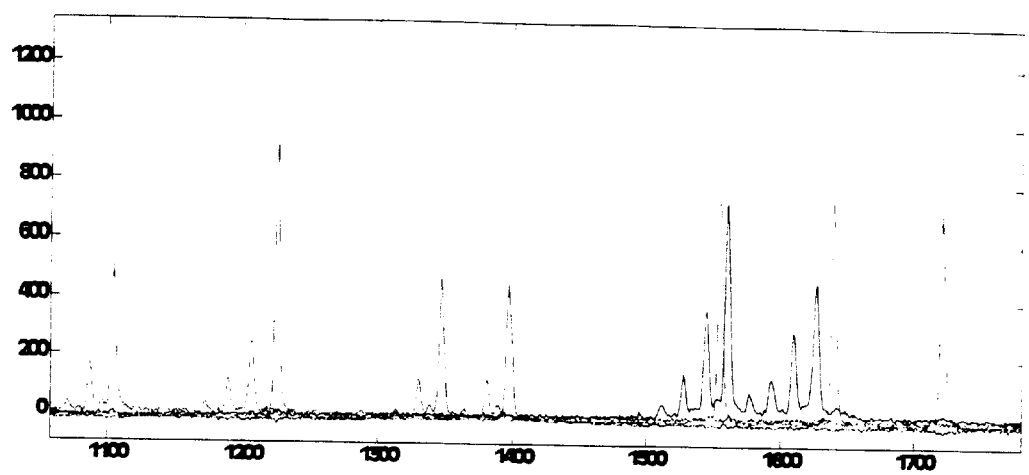
FIG. 8 is an exemplary graph of spectral calibration performed using the Type I method.

FIG. 8 is an exemplary graph of spectral calibration performed using the Type I method. The vertical axis represents arbitrary intensity units in the multicomponent, transformed signals (i.e., representing dye-labeled component concentration). The horizontal axis represents time-of-detection. This particular graph resulted from spectral calibration performed on the ABI GeneScan™ control sample by a conventional 3700 instrument. This data shows the raw data transformed to show the source signals. The method performs the transformation using the pseudo-inverse of the calibration (mixing) matrix on the same raw data. The flat baseline under the peaks indicates the low level of systematic error in the calibration.

Figure 9:
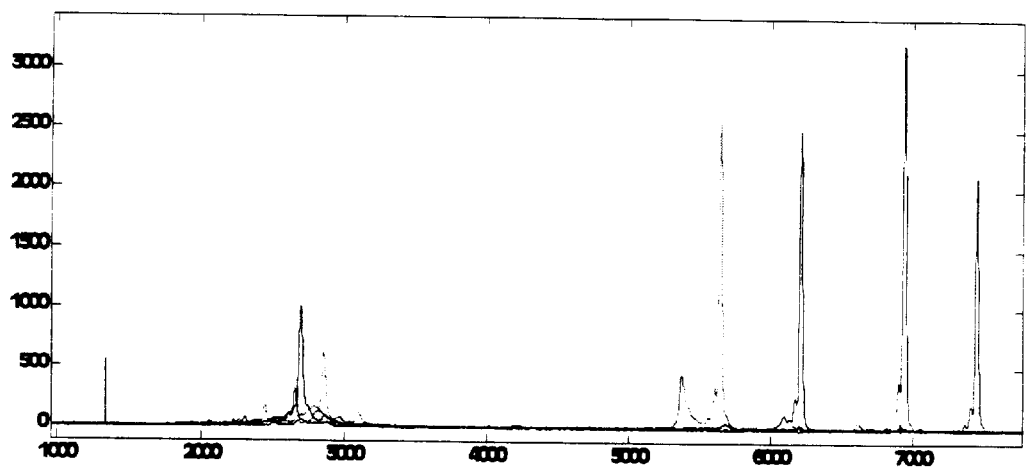
FIG. 9 is another exemplary graph of spectral calibration performed using the Type I method.

FIG. 9 is another exemplary graph of spectral calibration performed using the Type I method. The vertical axis represents arbitrary intensity units in the multicomponent, transformed signals (i.e., representing dye-labeled component concentration). The horizontal axis represents time-of-detection.

This data is analogous to the data in FIG. 8, but this data is obtained from the ABI 3700 matrix standard for conventional BigDye Terminator™ sequencing. This product is designed for single source peaks to elute in a particular order, but the method does not require knowledge of this information. Note that the method is robust against "flaws" in the data appearing before sample 4000 in FIG. 9.

Figure 10:
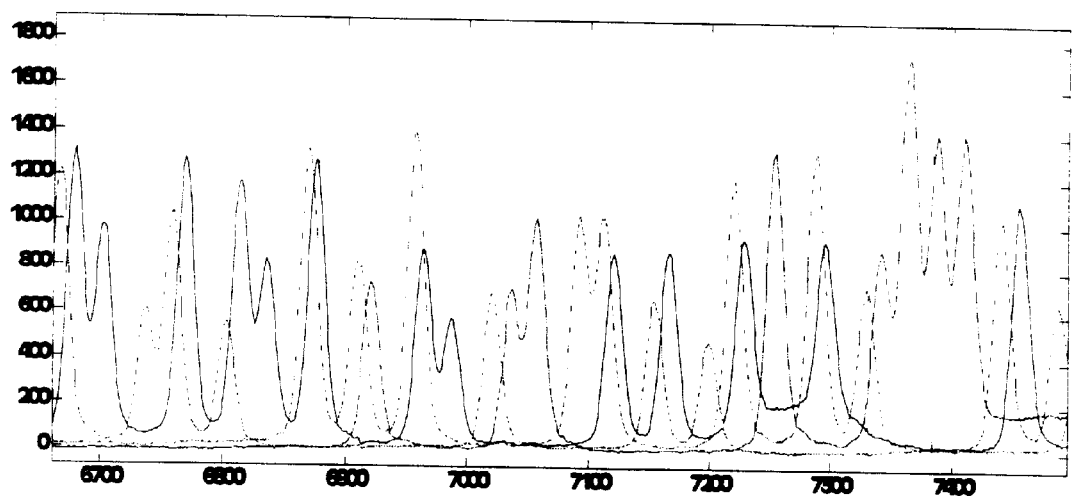
FIG. 10 is an exemplary graph of spectral calibration performed using the Type II method.

FIG. 10 is an exemplary graph of spectral calibration performed using the Type II method. The vertical axis represents arbitrary intensity units in the multicomponent, transformed signals (i.e., representing dye-labeled component concentration). The horizontal axis represents time-of-detection. This graph includes data that results from a calibration run on an ABI BigDye Terminator™ long-read sequencing standard (HSP69). The data includes the source signals obtained by applying the pseudo-inverse of the calibration matrix. The flat baseline evident in all color channels in regions where there are no peaks indicates the high quality of the result.

CONCLUSION

Systems and methods consistent with the present invention perform spectral calibration to identify regions in an electropherogram that have a spectral response characteristic of one or more spectrally-distinguishable molecular species. The systems and methods provide more accurate and more robust results over conventional systems.

The foregoing description of preferred embodiments of the present invention provides illustration and description, but is not intended to be exhaustive or to limit the invention to the precise form disclosed. Modifications and variations are possible in light of the above teachings or may be acquired from practice of the invention. For example, although a series of steps have been provided with regard to the flowcharts of FIGS. 3–7, the order of the steps does not matter.

In addition, systems and methods consistent with the present invention may be used to operate instruments in a self-calibrating mode. As a result, it is possible to do "on-the-fly" spectral calibration on individual samples or groups of samples collected during production runs. Certain dye sets, particularly those whose calibration matrices have high condition numbers, tend to require frequent calibration and are prone to introducing uncaught systematic errors if the calibration is slightly off. This can occur due to changes in temperature, mechanical misadjustment, etc. Furthermore, instruments, such as the conventional ABI 377 instrument, that collect data using a mechanical scanning mechanism may benefit from a dynamic calibration, since in this configuration a misalignment of the laser can introduce a resulting spectral shift from one side of a gel to the other. The existence of reliable on-the-fly calibration methods may alleviate these problems.

The scope of the invention is defined by the claims and their equivalents.

Appendix A: Detailed Explanations of Various Processing Methods

A.1 Noise Estimation

Noise estimation produces an estimate of the level of white noise contaminating the signal of interest. This may be used, for example, to convert threshold parameters from a dimensionless ratio (e.g. minimum signal-to-noise level) to an absolute intensity value. Noise estimation for each color channel of the electropherogram signals may be accomplished by various methods. Assuming that the noise is distributed normally as $N(0,\sigma)$, possible methods include:

1. Determining the variance of a de-biased region of the data that is known by previous experience to be free of signal.
2. Determining the high-frequency region of the power spectral density of the data. In the absence of high-frequency signal components, the high-frequency power spectral density can be related analytically to $\sigma$.
3. Determining a histogram of the difference signal squared, $d_i \equiv (y_{i+1}-y_i)^2$ using a predetermined bin size. The location of the initial peak in the distribution of $d_i$ can be related analytically to $\sigma$, provided that a sufficient portion of the data is free of non-noise contributions.

A.2 Peak Width Estimation

Peak width estimation involves discriminating between peaks of interest and "noise" peaks (e.g. flaws in the collected data not associated with actual fragments of interest). It may also be used to set appropriate values for parameters required by various other methods, such as the peak detection method (see A.4), window size for the baseline estimation and subtraction method (see A.3), etc.

In the simplest implementation, for example, for a system in which the electrophoresis parameters remain relatively constant, the width estimate can be set as a constant value, entered by a user. In another implementation, if the peak shape in the time/space domain of the electropherogram can be modeled (e.g., as a Gaussian), a Fourier transform of the data can estimate the width. The relationship between a signal consisting of a sequence of Gaussian peaks of width w and the shape of the power spectrum computed by Fourier transform of the signal may be derived mathematically.

A.3 Baseline Estimation and Subtraction

Baseline estimation and subtraction involve removing the background fluorescence signal from each color channel (i.e., virtual filter) of an electropherogram. To do this, it is typically assumed that the background is "slowly varying" as compared to the intensity variations caused by the passage of a labeled fragment, such as a DNA fragment (i.e., the peaks). A simple method for baseline estimation in each color channel may involve:

1. Defining a subwindow of length L that covers samples [1:L] in the data.
2. Computing the minimum value in the window.
3. Assigning this value to be the baseline estimate at the sample number corresponding to the center of the subwindow. If this is the first subwindow in the data, assign this value as the first L/2 baseline estimates. If this is the last subwindow in the data, assign this value as the last L/2 baseline estimates.
4. Incrementing the starting point of the subwindow by one. If the last point in the subwindow is greater than the number of samples, stop. Otherwise, go to step 2.

Variations of this method may include using something other than the minimum value, such as the median of some lowest percentile of the intensity values in the window. Alternative methods for subtracting baseline may include: (1) fitting polynomial or other models to local-minimum values in a region; and (2) methods based on iteratively subtracting a low-pass filtered version of the data from itself and clipping negative values.

A.4 Peak Detection

A method for peak detection may use Savitsky-Golay filtering for the computation of the numerical first derivative of the signal. A search for first derivative zero-crossing points (transition from positive value to negative value) provides the basic "peak" detection mechanism. Extensions of this basic method may include (1) filtering peaks based on an estimation of their width, (2) filtering peaks based on their amplitude, etc.

A.5 Rank Estimation

Rank analysis involves estimating the number of independent components exhibited in a block of electropherogram data. A method to do this may rely on the computation of singular values using SVD.

A simple method to estimate rank includes determining the number of singular values that lie above a threshold. The threshold may be determined based on an estimation of the noise (see A.1), the size of the data block considered, and an input minimum signal-to-noise level. An alternative method involves determining the differences in singular values sorted in descending order. Let $\vec{v}$ be the vector of sorted singular values, such that $v_1$ is the largest and $v_{n_b}$ is the smallest. Define the vector $\vec{\Delta}$ with elements $\Delta_j \equiv |v_{j+1}-v_j|$. The rank is computed as $r=\text{index\_of\_max}(\vec{\Delta})$. In other words, if $\max(\vec{\Delta})=\Delta_j$, then $r=j$.

A.6 Optimal Factor Selection

Optimal factor selection may be used when the number of factors located in the data (e.g., by cluster analysis) is greater than the expected number $n_d$, the number of dyes. The following method may be used under the assumption that the over-determination is caused by one or more regions of highly in-phase overlap between two distinct dye peaks. If two identically-shaped peaks representing distinct dye-labeled fragments overlap exactly in the time domain of the electropherogram, they will appear to the profile peak detection and rank analysis methods erroneously as a region of a single dye component.

A method may be used to determine which subset of $n_d$ factors in a set of M candidates is the best solution for the target dye set. The method may find the set of $n_d$ for which arbitrary linear combinations of pairs drawn from the set can best form the remaining candidate factors outside the set under the constraint that the mixing contributions must be positive coefficients.

For each unique set of $n_d$ basis functions formed from the M candidate functions, the method computes Score, then takes the set with the minimum Score. Score is computed as follows:

For each basis function $\vec{f}^{(j)}$ outside the candidate set of nd basis functions, $D_j$=inf;

For each unique pair $[\vec{a},\vec{b}]$ of normalized basis functions in the set, Compute Min_Constrained_Distance d of $\vec{f}^{(j)}$ from $[\vec{a},\vec{b}]$.

$D_j$=min(d,$D_j$);

$$Score = \sum_j D_j.$$

The Min_Constrained_Distance may be determined as follows:

Let $\vec{g}$ be the projection of $\vec{f}^{(j)}$ onto the 2-dimensional subspace formed by the pair $[\vec{a},\vec{b}]$;

Decompose $\vec{g}$ as $\vec{g}=c_a\vec{a}+c_b\vec{b}$, for example using the Gram-Schmidt process (as described in T. Apostol, "Calculus," Vol. II, Second Ed., pp. 22–30, 1969);

Re-define $c_a$=max(0,$c_a$);
Re-define $c_b$=max(0,$c_b$);
Re-compute $\vec{g}=c_a\vec{a}+c_b\vec{b}$ and compute $\vec{\delta}=\vec{f}^{(j)}-\vec{g}$;
Min_Constrained_Distance$\equiv\sqrt{\vec{\delta}\cdot\vec{\delta}}$.

This method may produce erroneous results if, for example, the initial over-determination is caused by contamination from N-M dye-labeled fragments outside of the target set, and not by peak overlap.

Appendix B: Hyperplane Intersection for Factor Computation from Pair of BMRs

This method requires that two binary mixture regions have been identified in the data. When these two regions are combined, rank analysis indicates that exactly three factors, or independent components, are present. Therefore, the two BMRs must share a common factor. The output of this method is the best answer for that factor, according to an optimization criterion.

Figure 11:
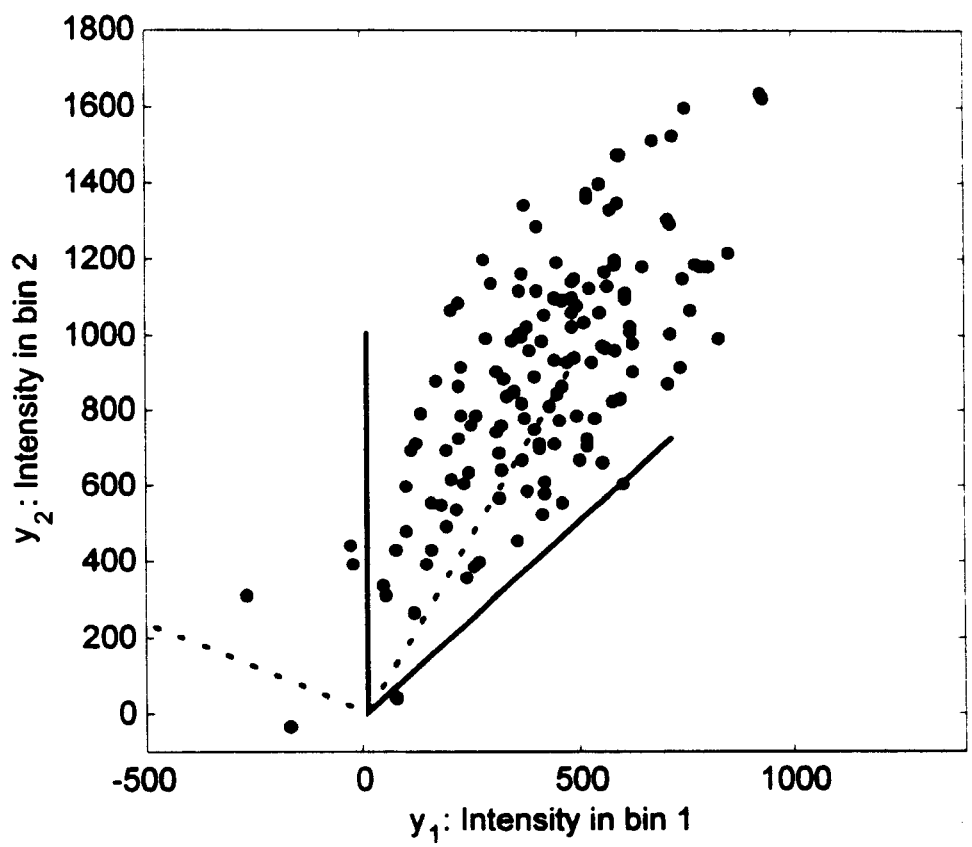
FIG. 11 is an example of a random mixture of two components in two dimensions.

FIG. 11 is an example of a random mixture of two components in two dimensions. The underlying components are the two vectors v1=[0,1] and v2=(1/√2)×[1,1], shown as solid lines. The data shown as dots are y=x1*v1+x2*v2, where the amplitudes x1 and x2 each consist of 200 values chosen from normal distributions N($\mu$,$\sigma$)=N(500,100) and N(600,200) respectively. The two direction vectors output from a conventional process that solves a linear system of equations, such as singular value decomposition (SVD), on the data y are shown as dotted lines.

As illustrated by the example in FIG. 11, the SVD process does not return the underlying (independent) components of an arbitrary binary mixture. Instead, SVD returns direction vectors which are always orthogonal. The first vector describes the direction of maximum variation in the data. In this illustrative example, the vector space is of dimension $n_b$, the number of spectral bins. In a vector space of higher dimensionality, although SVD will not produce the underlying independent components of a BMR, it will compute two direction vectors that span the same hyperplane as those components. This holds in the same (mean-square) sense as it does in the conventional Principle Component Analysis (PCA), described in A. Hyvarinen, "Survey on Independent Component Analysis," Neural Computing Surveys, 2:94–128, 1999, to the extent that the signal is a true BMR. Any deviation in the data from the 2-dimensional (hyperplane) subspace is presumed to be due to the presence of noise.

As an example, consider the case where $n_b$=3. Suppose that there are three dyes, and consider an instance where two BMRs consist of R1=(dyeA+dyeB) and R2=(dyeA+dyeC). In this case, SVD can be used to first extract orthogonal pairs of direction vectors that span the two planes. Let the two pairs of vectors be denoted as ($\hat{e}^{(1)},\hat{e}^{(2)}$) from R1 and ($\hat{e}^{(3)},\hat{e}^{(4)}$) from R2. Now, the desired result (the direction vector equivalent to the normalized spectrum of dyeA) is solved as the intersection of the two planes spanned by the two pairs of vectors. In this three-dimensional example, the solution for the factor would be explicit, because any two non-parallel planes in three dimensions intersect along a line.

For $n_b$>3, the situation is slightly more complicated but conceptually the same. Again, let us consider, for example, that the input includes intensity data from two BMRs, whose underlying dye content is R1=(dyeA+dyeB) and R2=(dyeA+dyeC). Use SVD or an equivalent data reduction technique to compute two sets of orthogonal direction vectors which span the two hyperplanes, ($\hat{e}^{(1)},\hat{e}^{(2)}$) spanning R1 and ($\hat{e}^{(3)},\hat{e}^{(4)}$) spanning R2. Since the data is no longer in three dimensions and is noisy, these hyperplanes do not necessarily intersect in a common line. The two hyperplanes do, however, "almost" intersect if they share a common factor. The unit-vector that is in some sense "closest" to both hyperplanes simultaneously is the optimal solution for the common spectrum of dyeA. This statement can be formulated and solved as a linear optimization problem as follows.

Denote the solution unit vector as $\hat{x}$. This will be the output of the process and in the example above would be a solution for the normalized spectrum of dyeA.

Compute the unit vectors ($\hat{e}^{(1)},\hat{e}^{(2)}$) using, for example, SVD on the de-biased data Z in region R1.

Compute the unit vectors ($\hat{e}^{(3)},\hat{e}^{(4)}$) using, for example, SVD on the de-biased data Z in region R2.

Define $s_{12}$ as the generalized distance from $\hat{x}0$ to the ($\hat{e}^{(1)},\hat{e}^{(2)}$) hyperplane,
$s_{12}^2=|(\hat{x}\cdot\hat{e}^{(1)})\hat{e}^{(1)}+(\hat{X}\cdot\hat{e}^{(2)})\hat{e}^{(2)}|^2=(\hat{x}\cdot\hat{e}^{(1)})^2+(\hat{x}\cdot\hat{e}^{(2)})^2$.

Similarly, define $s_{34}$ as the distance from $\hat{x}$ to the ($\hat{e}^{(3)},\hat{e}^{(4)}$) hyperplane,
$s_{34}^2=|(\hat{x}\cdot\hat{e}^{(3)})\hat{e}^{(3)}+(\hat{x}\cdot\hat{e}^{(4)})\hat{e}^{(4)}|^2=(\hat{x}\cdot\hat{e}^{(3)})^2+(\hat{x}\cdot\hat{e}^{(4)})^2$.

Minimize the sum of squared distances, $s^2\equiv s_{12}^2+s_{34}^2$. To do this, Set derivative to zero:

$$\frac{1}{2}\frac{\partial s^2}{\partial x_k} = \sum_i (\hat{x}\cdot\hat{e}^{(i)})e_k^{(i)} = 0.$$

Expanding dot products in the summation expression above and regrouping terms leads to the homogeneous system of equations, $A\hat{x}=0$, where the matrix A is defined as $$A_{kj} = \sum_i e_k^{(i)}e_j^{(i)}.$$

Solve the system of equations $A\hat{x}=0$ using, for example, SVD. The SVD decomposes the matrix A as $A=U\cdot S\cdot V^T$, where S is the diagonal matrix of singular values. The solution for $\hat{x}$ is given by the first column of the matrix V.

What is claimed is:

1. A computer-implemented method for performing spectral calibration, comprising:
   collecting data from monitoring an analytical separation of a plurality of spectrally-distinguishable molecular species;
   creating a data matrix from the collected data, each element in the data matrix representing a signal intensity at a particular time and over a particular range of light wavelengths or an approximated time-derivative of the signal intensity;
   identifying regions in the data matrix having spectral response characteristics of at least one of the molecular species by performing rank analysis on portions of the data matrix;
   determining a set of pure component spectral responses from the identified regions;
   grouping similar pure component spectral responses into clusters;
   determining a representative spectral response for each of the clusters; and
   correlating the representative spectral response for each of the clusters with one of the molecular species.

2. The computer-implemented method of claim 1, wherein the identifying regions includes:
   determining a profile equal to a sum of intensity values in the data matrix,
   detecting peaks in the profile, and
   selecting peaks exceeding a predetermined threshold.

3. The computer-implemented method of claim 2, wherein the detecting peaks includes:
   locating inflection points in the profile.

4. The computer-implemented method of claim 2, wherein the selecting peaks includes:
   identifying peaks having a width greater than the threshold.

5. The computer-implemented method of claim 2, wherein the selecting peaks includes:
   identifying peaks having a height greater than the threshold.

6. The computer-implemented method of claim 1, wherein the identifying regions includes:
   determining a profile equal to a sum of intensity values in the data matrix,
   detecting peaks in the profile,
   estimating a number of pure component spectral responses represented in a region around each of the detected peaks, and
   selecting ones of the regions having a predetermined estimated number of pure component spectral responses.

7. The computer-implemented method of claim 1, wherein the identifying regions includes:
   determining a rank for each portion or overlapping portions of the data matrix, the rank estimating a number of pure component spectral responses associated with each of the portions, and
   selecting ones of the portions having a predetermined estimated number of pure component spectral responses.

8. The computer-implemented method of claim 1, wherein the grouping includes:
   associating similar spectral responses from the determined set using one of a partitional clustering process and a hierarchical clustering structure.

9. The computer-implemented method of claim 8, wherein the associating includes:
   selecting an optimal number of clusters using at least one of input parameters and heuristics.

10. The computer-implemented method of claim 1, wherein the determining a representative spectral response includes:
    defining a vector-valued function of an arbitrary number of input spectral response functions to obtain an optimal spectral response function as the representative spectral response for each of the clusters.

11. The computer-implemented method of claim 10, wherein the defining a vector-valued function includes:
    identifying one of a mean, weighted mean, median, and middle percentile range for each of the clusters, and
    using the identified mean, weighted mean, median, or middle-percentile range as the representative spectral response for the cluster.

12. The computer-implemented method of claim 10, wherein the defining a vector-valued function includes:
    solving a minimization criterion on data in each of the clusters to determine the representative spectral response for the cluster.

13. The computer-implemented method of claim 10, wherein the defining a vector-valued function includes:
    solving a Principle Component Analysis on data in each of the clusters to determine the representative spectral response for the cluster.

14. The computer-implemented method of claim 1, wherein the correlating includes:
    classifying the spectral responses as one of a pure-dye response, a response due to spurious fluorescence, detection noise, and a mixed dye response, and
    selecting a predetermined number of the classified spectral responses.

15. The computer-implemented method of claim 14, wherein the classifying includes:
    applying a heuristic or filtering process to eliminate at least one of the spectral responses.

16. The computer-implemented method of claim 14, wherein the classifying includes:
    determining whether a number of candidate representative spectral responses exceeds a predetermined number, and
    eliminating ones of the candidate representative spectral responses that exceed the predetermined number.

17. The computer-implemented method of claim 1, wherein the correlating the representative spectral response includes:
using a convention to relate each of the molecular species to a light wavelength order of maximum emission, and
mapping each of the representative spectral responses to the molecular species according to the convention.

18. The computer-implemented method of claim 1, further comprising:
generating a calibration matrix based on a result of the correlation; and
comparing a property of the calibration matrix with an expected range to perform error detection.

19. A system for performing spectral calibration, comprising:
collecting data from monitoring an analytical separation of a plurality of spectrally-distinguishable molecular species;
creating a data matrix from the collected data, each element in the data matrix representing a signal intensity at a particular time and over a particular range of light wavelengths or an approximated time-derivative of the signal intensity;
identifying regions in the data matrix having spectral response characteristics of at least one of the molecular species by performing rank analysis on portions of the data matrix;
determining a set of pure component spectral responses from the identified regions;
grouping similar pure component spectral responses into clusters;
determining a representative spectral response for each of the clusters; and
correlating the representative spectral response for each of the clusters with one of the molecular species.

20. A system for performing spectral calibration, comprising:
a memory configured to store instructions; and
a processor configured to execute the instructions stored in the memory to collect data from monitoring an analytical separation of a plurality of spectrally-distinguishable molecular species, create a data matrix from the collected data, each element in the data matrix representing a signal intensity at a particular time and over a particular range of light wavelengths or an approximated time-derivative of the signal intensity, identify regions in the data matrix having spectral response characteristics of at least one of the molecular species by performing rank analysis on portions of the data matrix, determine a set of pure component spectral responses from the identified regions, group similar pure component spectral responses into clusters, determine a representative spectral response for each of the clusters, and correlate the representative spectral response for each of the clusters with one of the molecular species.

21. The system of claim 20, wherein when identifying the regions, the processor is further configured to determine a profile equal to a sum of intensity values in the data matrix, detect peaks in the profile, and select peaks exceeding a predetermined threshold.

22. The system of claim 21, wherein when detecting the peaks, the processor is further configured to locate inflection points in the profile.

23. The system of claim 21, wherein when selecting the peaks, the processor is further configured to identify peaks having a width greater than the threshold.

24. The system of claim 21, wherein when selecting the peaks, the processor is further configured to identify peaks having a height greater than the threshold.

25. The system of claim 20, wherein when identifying the regions, the processor is further configured to determine a profile equal to a sum of intensity values in the data matrix, detect peaks in the profile, estimate a number of pure component spectral responses represented in a region around each of the detected peaks, and select ones of the regions having a predetermined estimated number of pure component spectral responses.

26. The system of claim 20, wherein when identifying the regions, the processor is further configured to determine a rank for each portion or overlapping portion of the data matrix, the rank estimating a number of pure component spectral responses associated with each of the portions, and select ones of the portions having a predetermined estimated number of pure component spectral responses.

27. The system of claim 20, wherein when grouping, the processor is configured to associate similar spectral responses from the determined set using one of a partitional clustering process and a hierarchical clustering structure.

28. The system of claim 27, wherein when associating, the processor is configured to select an optimal number of clusters using at least one of input parameters and heuristics.

29. The system of claim 20, wherein when determining a representative spectral response, the processor is configured to define a vector-valued function of an arbitrary number of input spectral response functions to obtain an optimal spectral response function as the representative spectral response for each of the clusters.

30. The system of claim 29, wherein when defining a vector-valued function, the processor is configured to identify one of a mean, weighted mean, median, and middle percentile range for each of the clusters, and use the identified mean, weighted mean, median, or middle-percentile range as the representative spectral response for the cluster.

31. The system of claim 29, wherein when defining a vector-valued function, the processor is configured to solve a minimization criterion on data in each of the clusters to determine the representative spectral response for the cluster.

32. The system of claim 29, wherein when defining a vector-valued function, the processor is configured to solve a Principle Component Analysis on data in each of the clusters to determine the representative spectral response for the cluster.

33. The system of claim 20, wherein when correlating, the processor is configured to classify the spectral responses as one of a pure-dye response, a response due to spurious fluorescence, detection noise, and a mixed dye response, and select a predetermined number of the classified spectral responses.

34. The system of claim 33, wherein when classifying, the processor is configured to apply a heuristic or filtering process to eliminate at least one of the spectral responses.

35. The system of claim 33, wherein when classifying, the processor is configured to determine whether a number of candidate representative spectral responses exceeds a predetermined number, and eliminate ones of the candidate representative spectral responses that exceed the predetermined number.

36. The system of claim 20, wherein when correlating the representative spectral response, the processor is configured to use a convention to relate each of the molecular species to a light wavelength order of maximum emission, and map each of the representative spectral responses to the molecular species according to the convention.

37. The system of claim 20, wherein the processor is further configured to generate a calibration matrix based on a result of the correlation, and compare a property of the calibration matrix with an expected range to perform error detection.

38. A computer-readable medium storing instructions executable by a processor for performing a spectral calibration method, the method comprising:
    collecting data from monitoring an analytical separation of a plurality of spectrally-distinguishable molecular species;
    creating a data matrix from the collected data, each element in the data matrix representing a signal intensity at a particular time and over a particular range of light wavelengths or an approximated time-derivative of the signal intensity;
    identifying regions in the data matrix having spectral response characteristics of at least one of the molecular species by performing rank analysis on portions of the data matrix;
    determining a set of pure component spectral responses from the identified regions;
    grouping similar pure component spectral responses into clusters;
    determining a representative spectral response for each of the clusters; and
    correlating the representative spectral response for each of the clusters with one of the molecular species.

39. The computer-readable medium of claim 38, wherein the identifying regions includes:
    determining a profile equal to a sum of intensity values in the data matrix,
    detecting peaks in the profile, and
    selecting peaks exceeding a predetermined threshold.

40. The computer-readable medium of claim 39, wherein the detecting peaks includes:
    locating inflection points in the profile.

41. The computer-readable medium of claim 39, wherein the selecting peaks includes:
    identifying peaks having a width greater than the threshold.

42. The computer-readable medium of claim 39, wherein the selecting peaks includes:
    identifying peaks having a height greater than the threshold.

43. The computer-readable medium of claim 38, wherein the identifying regions includes:
    determining a profile equal to a sum of intensity values in the data matrix,
    detecting peaks in the profile,
    estimating a number of pure component spectral responses represented in a region around each of the detected peaks, and
    selecting ones of the regions having a predetermined estimated number of pure component spectral responses.

44. The computer-readable medium of claim 38, wherein the identifying regions includes:
    determining a rank for each portion or overlapping portions of the data matrix, the rank estimating a number of pure component spectral responses associated with each of the portions, and
    selecting ones of the portions having a predetermined estimated number of pure component spectral responses.

45. The computer-readable medium of claim 38, wherein the grouping includes:
    associating similar spectral responses from the determined set using one of a partitional clustering process and a hierarchical clustering structure.

46. The computer-readable medium of claim 45, wherein the associating includes:
    selecting an optimal number of clusters using at least one of input parameters and heuristics.

47. The computer-readable medium of claim 38, wherein the determining a representative spectral response includes:
    defining a vector-valued function of an arbitrary number of input spectral response functions to obtain an optimal spectral response function as the representative spectral response for each of the clusters.

48. The computer-readable medium of claim 47, wherein the defining a vector-valued function includes:
    identifying one of a mean, weighted mean, median, and middle percentile range for each of the clusters, and
    using the identified mean, weighted mean, median, or middle-percentile range as the representative spectral response for the cluster.

49. The computer-readable medium of claim 47, wherein the defining a vector-valued function includes:
    solving a minimization criterion on data in each of the clusters to determine the representative spectral response for the cluster.

50. The computer-readable medium of claim 47, wherein the defining a vector-valued function includes:
    solving a Principle Component Analysis on data in each of the clusters to determine the representative spectral response for the cluster.

51. The computer-readable medium of claim 38, wherein the correlating includes:
    classifying the spectral responses as one of a pure-dye response, a response due to spurious fluorescence, detection noise, and a mixed dye response, and
    selecting a predetermined number of the classified spectral responses.

52. The computer-readable medium of claim 51, wherein the classifying includes:
    applying a heuristic or filtering process to eliminate at least one of the spectral responses.

53. The computer-readable medium of claim 51, wherein the classifying includes:
    determining whether a number of candidate representative spectral responses exceeds a predetermined number, and
    eliminating ones of the candidate representative spectral responses that exceed the predetermined number.

54. The computer-readable medium of claim 38, wherein the correlating the representative spectral response includes:
    using a convention to relate each of the molecular species to a light wavelength order of maximum emission, and
    mapping each of the representative spectral responses to the molecular species according to the convention.

55. The computer-readable medium of claim 38, further comprising:
    generating a calibration matrix based on a result of the correlation; and
    comparing a property of the calibration matrix with an expected range to perform error detection.

56. An apparatus for performing spectral calibration, comprising:

a light separator that spatially separates wavelengths of light representing a plurality of spectrally-distinguishable molecular species;

a spectral array detector that generates data relating to intensity as a function of the wavelengths separated by the light separator; and a processor that collects the data from the spectral array detector, creates a data matrix from the collected data, each element in the data matrix representing a signal intensity at a particular time and over a particular range of light wavelengths or an approximated time-derivative of the signal intensity, identifies regions in the data matrix having spectral response characteristics of at least one of the molecular species by performing rank analysis on portions of the data matrix, determines a set of pure component spectral responses from the identified regions, groups similar pure component spectral responses into clusters, determines a representative spectral response for each of the clusters, and correlates the representative spectral response for each of the clusters with one of the molecular species.

57. A computer-implemented method for performing spectral calibration, comprising:

collecting data from monitoring an analytical separation of a plurality of spectrally-distinguishable molecular species;

creating a data matrix from the collected data, each element in the data matrix representing a signal intensity at a particular time and a particular range of wavelengths of light or an approximated time-derivative of the signal intensity;

identifying binary mixture regions within the data matrix;

determining pairs of the binary mixture regions that contain one common spectral response;

identifying a component that represents the one common spectral response using data in the determined pairs;

grouping the one common spectral response from each of the determined pairs into clusters;

determining a representative spectral response for each of the clusters; and correlating the representative spectral response for each of the clusters with one of the molecular species.

58. The computer-implemented method of claim 57, wherein the identifying binary mixture regions includes:

determining a rank for each portion or overlapping portions of the data matrix, the rank estimating a number of pure component spectral responses associated with each of the portions, and selecting ones of the portions having a predetermined estimated number of pure component spectral responses.

59. The computer-implemented method of claim 57, wherein the identifying a component includes:

using a geometric solution to identify the component.

60. The computer-implemented method of claim 57, wherein the grouping includes:

associating similar spectral responses from the determined set using one of a partitional clustering process and a hierarchical clustering structure.

61. The computer-implemented method of claim 60, wherein the associating includes:

selecting an optimal number of clusters using at least one of input parameters and heuristics.

62. The computer-implemented method of claim 57, wherein the determining a representative spectral response includes:

defining a vector-valued function of an arbitrary number of input spectral response functions to obtain an optimal spectral response function as the representative spectral response for each of the clusters.

63. The computer-implemented method of claim 62, wherein the defining a vector-valued function includes:

identifying one of a mean, weighted mean, median, and middle percentile range for each of the clusters, and using the identified mean, weighted mean, median, or middle-percentile range as the representative spectral response for the cluster.

64. The computer-implemented method of claim 62, wherein the defining a vector-valued function includes:

solving a minimization criterion on data in each of the clusters to determine the representative spectral response for the cluster.

65. The computer-implemented method of claim 62, wherein the defining a vector-valued function includes:

solving a Principle Component Analysis on data in each of the clusters to determine the representative spectral response for the cluster.

66. The computer-implemented method of claim 57, wherein the correlating includes:

classifying the spectral responses as one of a pure-dye response, a response due to spurious fluorescence, detection noise, and a mixed dye response, and selecting a predetermined number of the classified spectral responses.

67. The computer-implemented method of claim 66, wherein the classifying includes:

applying a heuristic or filtering process to eliminate at least one of the spectral responses.

68. The computer-implemented method of claim 66, wherein the classifying includes:

determining whether a number of candidate representative spectral responses exceeds a predetermined number, and eliminating ones of the candidate representative spectral responses that exceed the predetermined number.

69. The computer-implemented method of claim 57, wherein the correlating the representative spectral response includes:

using a convention to relate each of the molecular species to a light wavelength order of maximum emission, and mapping each of the representative spectral responses to the molecular species according to the convention.

70. The computer-implemented method of claim 57, further comprising:

generating a calibration matrix based on a result of the correlation; and comparing a property of the calibration matrix with an expected range to perform error detection.

71. A system for performing spectral calibration, comprising:

means for collecting data from monitoring an analytical separation of a plurality of spectrally-distinguishable molecular species;

means for creating a data matrix from the collected data, each element in the data matrix representing a signal intensity at a particular time and a particular range of wavelengths of light or an approximated time-derivative of the signal intensity;

means for identifying binary mixture regions within the data matrix;

means for determining pairs of the binary mixture regions that contain one common spectral response;

means for identifying a component that represents the one common spectral response using data in the determined pairs;

means for grouping the one common spectral response from each of the determined pairs into clusters;

means for determining a representative spectral response for each of the clusters; and means for correlating the representative spectral response for each of the clusters with one of the molecular species.

72. A system for performing spectral calibration, comprising:

a memory configured to store instructions; and a processor configured to execute the instructions in the memory to collect data from monitoring an analytical separation of a plurality of spectrally-distinguishable molecular species, create a data matrix from the collected data, each element in the data matrix representing a signal intensity at a particular time and a particular range of wavelengths of light or an approximated time-derivative of the signal intensity, identify binary mixture regions within the data matrix, determine pairs of the binary mixture regions that contain one common spectral response, identify a component that represents the one common spectral response using data in the determined pairs, group the one common spectral response from each of the determined pairs into clusters, determine a representative spectral response for each of the clusters, and correlate the representative spectral response for each of the clusters with one of the molecular species.

73. The system of claim 72, wherein when identifying the binary mixture regions, the processor is configured to determine a rank for each portion or overlapping portions of the data matrix, the rank estimating a number of pure component spectral responses associated with each of the portions, and select ones of the portions having a predetermined estimated number of pure component spectral responses.

74. The system of claim 72, wherein when identifying a component, the processor is configured to use a geometric solution to identify the component.

75. The system of claim 72, wherein when grouping, the processor is configured to associate similar spectral responses from the determined set using one of a partitional clustering process and a hierarchical clustering structure.

76. The system of claim 75, wherein when associating, the processor is configured to select an optimal number of clusters using at least one of input parameters and heuristics.

77. The system of claim 72, wherein when determining a representative spectral response, the processor is configured to define a vector-valued function of an arbitrary number of input spectral response functions to obtain an optimal spectral response function as the representative spectral response for each of the clusters.

78. The system of claim 77, wherein when defining a vector-valued function, the processor is configured to identify one of a mean, weighted mean, median, and middle percentile range for each of the clusters, and use the identified mean, weighted mean, median, or middle-percentile range as the representative spectral response for the cluster.

79. The system of claim 77, wherein when defining a vector-valued function, the processor is configured to solve a minimization criterion on data in each of the clusters to determine the representative spectral response for the cluster.

80. The system of claim 77, wherein when defining a vector-valued function, the processor is configured to solve a Principle Component Analysis on data in each of the clusters to determine the representative spectral response for the cluster.

81. The system of claim 72, wherein when correlating, the processor is configured to classify the spectral responses as one of a pure-dye response, a response due to spurious fluorescence, detection noise, and a mixed dye response, and select a predetermined number of the classified spectral responses.

82. The system of claim 81, wherein when classifying, the processor is configured to apply a heuristic or filtering process to eliminate at least one of the spectral responses.

83. The system of claim 81, wherein when classifying, the processor is configured to determine whether a number of candidate representative spectral responses exceeds a predetermined number, and eliminate ones of the candidate representative spectral responses that exceed the predetermined number.

84. The system of claim 72, wherein when correlating the representative spectral response, the processor is configured to use a convention to relate each of the molecular species to a light wavelength order of maximum emission, and map each of the representative spectral responses to the molecular species according to the convention.

85. The system of claim 72, wherein the processor is further configured to generate a calibration matrix based on a result of the correlation, and compare a property of the calibration matrix with an expected range to perform error detection.

86. A computer-readable medium storing instructions executable by a processor for performing a spectral calibration method, the method comprising:

collecting data from monitoring an analytical separation of a plurality of spectrally-distinguishable molecular species;

creating a data matrix from the collected data, each element in the data matrix representing a signal intensity at a particular time and a particular range of wavelengths of light or an approximated time-derivative of the signal intensity;

identifying binary mixture regions within the data matrix;

determining pairs of the binary mixture regions that contain one common spectral response;

identifying a component that represents the one common spectral response using data in the determined pairs;

grouping the one common spectral response from each of the determined pairs into clusters;

determining a representative spectral response for each of the clusters; and correlating the representative spectral response for each of the clusters with one of the molecular species.

87. The computer-readable medium of claim 86, wherein the identifying binary mixture regions includes:

determining a rank for each portion or overlapping portions of the data matrix, the rank estimating a number of pure component spectral responses associated with each of the portions, and selecting ones of the portions having a predetermined estimated number of pure component spectral responses.

88. The computer-readable medium of claim 86, wherein the identifying a component includes:

using a geometric solution to identify the component.

89. The computer-readable medium of claim 86, wherein the grouping includes:

associating similar spectral responses from the determined set using one of a partitional clustering process and a hierarchical clustering structure.

90. The computer-readable medium of claim 89, wherein the associating includes:

selecting an optimal number of clusters using at least one of input parameters and heuristics.

91. The computer-readable medium of claim 86, wherein the determining a representative spectral response includes:

defining a vector-valued function of an arbitrary number of input spectral response functions to obtain an optimal spectral response function as the representative spectral response for each of the clusters.

92. The computer-readable medium of claim 91, wherein the defining a vector-valued function includes:

identifying one of a mean, weighted mean, median, and middle percentile range for each of the clusters, and using the identified mean, weighted mean, median, or middle-percentile range as the representative spectral response for the cluster.

93. The computer-readable medium of claim 91, wherein the defining a vector-valued function includes:

solving a minimization criterion on data in each of the clusters to determine the representative spectral response for the cluster.

94. The computer-readable medium of claim 91, wherein the defining a vector-valued function includes:

solving a Principle Component Analysis on data in each of the clusters to determine the representative spectral response for the cluster.

95. The computer-readable medium of claim 86, wherein the correlating includes:

classifying the spectral responses as one of a pure-dye response, a response due to spurious fluorescence, detection noise, and a mixed dye response, and selecting a predetermined number of the classified spectral responses.

96. The computer-readable medium of claim 95, wherein the classifying includes:

applying a heuristic or filtering process to eliminate at least one of the spectral responses.

97. The computer-readable medium of claim 95, wherein the classifying includes:

determining whether a number of candidate representative spectral responses exceeds a predetermined number, and eliminating ones of the candidate representative spectral responses that exceed the predetermined number.

98. The computer-readable medium of claim 86, wherein the correlating the representative spectral response includes:

using a convention to relate each of the molecular species to a light wavelength order of maximum emission, and mapping each of the representative spectral responses to the molecular species according to the convention.

99. The computer-readable medium of claim 86, flirter comprising:

generating a calibration matrix based on a result of the correlation; and comparing a property of the calibration matrix with an expected range to perform error detection.

100. An apparatus for performing spectral calibration, comprising:

a light separator that spatially separates wavelengths of light representing a plurality of spectrally-distinguishable molecular species;

a spectral array detector that generates data relating to intensity as a function of the wavelengths separated by the light separator; and a processor that collects data from monitoring an analytical separation of a plurality of spectrally-distinguishable molecular species, creates a data matrix from the collected data, each element in the data matrix representing a signal intensity at a particular time and a particular range of wavelengths of light or an approximated time-derivative of the signal intensity, identifies binary mixture regions within the data matrix, determines pairs of the binary mixture regions that contain one common spectral response, identifies a component that represents the one common spectral response using data in the determined pairs, groups the one common spectral response from each of the determined pairs into clusters, determines a representative spectral response for each of the clusters, and correlates the representative spectral response for each of the clusters with one of the molecular species.

* * * * *

UNITED STATES PATENT AND TRADEMARK OFFICE
CERTIFICATE OF CORRECTION

PATENT NO. : 6,333,501 B1  
DATED : December 25, 2001  
INVENTOR(S) : James N. LaBrenz It is certified that error appears in the above-identified patent and that said Letters Patent is hereby corrected as shown below:

<u>Column 30, claim 99,</u>  
Line 12, "flirter" should read -- further --.

Signed and Sealed this

Twenty-sixth Day of March, 2002

Attest:

Attesting Officer

JAMES E. ROGAN  
*Director of the United States Patent and Trademark Office*